(12) United States Patent
Ho

(10) Patent No.: US 11,911,618 B2
(45) Date of Patent: Feb. 27, 2024

(54) BODY JOINT SUPPORT DEVICE WITH INFLATABLE AIRBAG, ELECTRODE OR BOTH

(71) Applicant: Hoi Ming Michael Ho, Tuen Mun (HK)

(72) Inventor: Hoi Ming Michael Ho, Tuen Mun (HK)

( * ) Notice: Subject to any disclaimer, the term of this patent is extended or adjusted under 35 U.S.C. 154(b) by 303 days.

(21) Appl. No.: 17/171,998

(22) Filed: Feb. 9, 2021

(65) Prior Publication Data

US 2022/0001178 A1 Jan. 6, 2022

(30) Foreign Application Priority Data

Jul. 3, 2020 (CN) .......................... 202010631822.5

(51) Int. Cl.
*A61N 1/36* (2006.01)
*A61F 5/01* (2006.01)
(Continued)

(52) U.S. Cl.
CPC .......... *A61N 1/36021* (2013.01); *A61F 5/012* (2013.01); *A61N 1/0484* (2013.01);
(Continued)

(58) Field of Classification Search
CPC .............. A61N 1/36021; A61N 1/0484; A61N 1/0492; A61F 5/012; A61F 5/34; A61F 5/0127; A61F 5/0125; A61F 5/01; A61H 2201/0207; A61H 2201/10; A61H 1/0262; A61H 3/00; A61H 2001/0233;
(Continued)

(56) References Cited

U.S. PATENT DOCUMENTS 5,387,185 A * 2/1995 Johnson, Jr. .......... A61F 5/0585
602/5
6,551,264 B1 * 4/2003 Cawley ................. A61F 5/0125
128/882
(Continued)

FOREIGN PATENT DOCUMENTS

EP 2033614 A1 3/2009
JP S58-12659 A 1/1983
(Continued)

*Primary Examiner* — Michael R Reid
*Assistant Examiner* — Nathan M Le
(74) *Attorney, Agent, or Firm* — CIPO IP Group

(57) ABSTRACT

A body joint support device capable of abutting against at least one body joint and accommodating in configuration both to the bending and non-bending states of the body joint includes a covering structure, a control device, and at least one electrode pad unit and/or inflatable airbag. The covering structure can be worn to the body joint, the electrode pad unit is provided on the inner surface of the covering structure, and the control device is provided on the outer surface of the covering structure. The control device can transmit current to the electrode pad unit so that the electrode pad unit outputs current to stimulate and/or heat muscles. When a body joint moves, the force produced by the covering structure can press the electrode pad unit tightly against the skin at the body joint, so that the electrode pad unit does not become loose due to frequent body joint movement.

20 Claims, 27 Drawing Sheets

(51) Int. Cl.
*A61N 1/04* (2006.01)
*A61F 7/02* (2006.01)

(52) U.S. Cl.
CPC ............. *A61F 2007/0228* (2013.01); *A61H 2201/0207* (2013.01); *A61H 2201/10* (2013.01); *A61N 1/0452* (2013.01); *A61N 1/0456* (2013.01)

(58) Field of Classification Search
CPC .. A61H 9/005; A61H 9/00078; A61H 9/0092; A61H 2007/0228; A61H 2007/0233
See application file for complete search history.

(56) References Cited

U.S. PATENT DOCUMENTS

| | | | | |
|---|---|---|---|---|
| 8,328,747 | B2* | 12/2012 | Matsunaga | A61F 5/0123 602/26 |
| 2010/0262052 | A1 | 10/2010 | Lunau | |
| 2011/0152983 | A1* | 6/2011 | Schirrmacher | A61F 7/02 607/104 |
| 2014/0039595 | A1 | 2/2014 | Kroll-Orywahl | |
| 2014/0083434 | A1* | 3/2014 | Groteke | A61N 1/0456 128/845 |
| 2017/0050020 | A1 | 2/2017 | Yang | |
| 2017/0189221 | A1* | 7/2017 | Fullerton | A43B 7/38 |
| 2017/0273830 | A1* | 9/2017 | Hitschmann | A61F 13/108 |
| 2018/0125693 | A1* | 5/2018 | Best | A61F 5/0109 |
| 2018/0221676 | A1* | 8/2018 | Patel | A61H 31/00 |
| 2018/0311493 | A1* | 11/2018 | Matsushita | A61N 1/0452 |
| 2019/0298998 | A1* | 10/2019 | Coleman | A61B 5/389 |

FOREIGN PATENT DOCUMENTS

| | | |
|---|---|---|
| JP | H08-511445 A | 12/1996 |
| JP | H24-2012061310 A | 3/2012 |
| JP | H30-2018510036 A | 4/2018 |

* cited by examiner

BODY JOINT SUPPORT DEVICE WITH INFLATABLE AIRBAG, ELECTRODE OR BOTH

CROSS-REFERENCE TO RELATED PATENT APPLICATION

This non-provisional application claims priority to and the benefit of, under 35 U.S.C. § 119(a), Chinese Patent Application No. 202010631822.5 filed in People's Republic of China on Jul. 3, 2020. The entire content of the above identified application is incorporated herein by reference.

FIELD

The present disclosure relates to a body joint support device, and more particularly to a body joint support device with at least one inflatable airbag and/or at least one electrode.

BACKGROUND

Traditionally, people suffering from injuries to their knee, ankle, shoulder, elbow, wrist or lower back may seek different treatments to alleviate the swelling and pain resulted from the injuries. For example, a patient may wear an orthopedic device to restrict the motion of an injured body part, seek compression therapy to reduce water retention and swelling, or seek electrotherapy to relieve pain and stimulate healing.

However, to receive different treatments can cost a patient a lot of time, and in turn cause great inconvenience to the patient. Moreover, based on years-experience in, and long-time attention to the development of, the technical field of the present disclosure, room for improvement for a conventional physiotherapy device in the following aspects has also come to attention of and are addressed in the present disclosure.

First, a traditional physiotherapy device such as a body joint support device has a relatively large size and needs to be placed at a fixed location, which makes its use less convenient. Second, when a user is alone by himself or herself, it is difficult for him or her to attach an electrode of a body joint support device precisely to his or her body locations such as the back of the shoulders, lower back or waist. Third, such a conventional electrode is attached to the skin purely by gel without resolving to other fixation means. Therefore, when a user is in a movement, frequent or large limp movement can very easily cause the surface of the conventional electrode to lose its full contact with the skin, even leading to its falling from the skin. Further, if the conventional electrode is not fully adhered to the skin, poor conduction ensues, which causes pin/needle-like pain to the patient and leads to ineffective therapy. Fourth, if the conventional electrode is adhered to the joints of the human body, such as waist, ankle, knee, elbow, shoulder, etc., the conventional electrode would be less likely to fully adhere to, and more likely to fall off from, the skin at these body parts, because these body pans during body movement have larger positional change and are prone to severe swinging. For example, when a conventional electrode is adhered to an ankle, walking or running would cause the skin corresponding to the ankle to frequently extend and shrink, and therefore can cause the electrode to fall off from the skin at the ankle.

In summary, seeking and receiving different treatments presently costs a patient a great deal of time and effort, and a conventional physiotherapy device has not been able to suffice user demand in the above-referenced aspects. Accordingly, the present disclosure aims to solve these aforementioned issues to provide a body joint support device that affords more convenience to the users.

SUMMARY

One aspect of the present disclosure is directed to a body joint support device. The body joint support device includes a covering structure, at least one electrode pad unit and a control device. The covering structure can be worn at at least one body joint and press a skin of the body joint that is in a bending state against an inner surface of the covering structure by a pressing force exerted by the covering structure. The at least one electrode pad unit is disposed on the inner surface of the covering structure, and can abut against the skin of the body joint through the pressing force. The control device can be fixed on the covering structure, and transmit current to the electrode pad unit for the electrode pad unit to transmit current to stimulate and/or heat muscle. Accordingly, the electrode pad unit can be tightly positioned on and abutted against the skin due to the force exerted by the covering structure without falling off from the body joint as could be caused by frequent activity of the body joint.

In certain embodiments, the covering structure includes a covering body, at least one airbag, at least one inflating device, and at least one adjusting strap. The electrode pad unit is disposed on an inner surface of the covering body, and the control device is disposed on an outer surface of the covering body. The at least one airbag is located in the covering body. The at least one airbag can expand along a direction toward the inner surface of the covering body, so that the inner surface of the covering body exerts the pressing force to the skin of the body joint. The at least one inflating device can be connected to the airbag, and inflate or deflate the airbag to change an expansion degree or deflation degree of the airbag. The at least one adjusting strap has one end connected to the covering body and another end provided with a fixation portion. The fixation portion can be fixed on an outer surface of the covering body and be pulled to press the inner surface of the covering body against the skin surface of the body joint.

In certain embodiments, the covering body includes a first sheet body and a second sheet body, the airbag is located between the first sheet body and the second sheet body, the electrode pad unit is disposed on the first sheet body, and the control device and the adjusting strap are disposed on the second sheet body.

In certain embodiments, the body joint support device further includes at least one angle adjustable support member. The at least one angle adjustable support member includes at least two plate bodies having an adjustable fixed angle therebetween. Each plate body has one end which can be inserted into a corresponding slot formed on the outer surface of the covering body.

In certain embodiments, the inflating device includes at least one air valve and an inflating member. The inflating member can be connected to the airbag through the air valve, and inflate or deflate the airbag.

In certain embodiments, the covering structure includes at least one elastic material, and can abut against the skin of the body joint by the elasticity of the covering structure when being worn at the body joint.

In certain embodiments, the covering structure is in a cylindrical shape and can be sleeved at the body joint.

In certain embodiments, the covering body includes a sheet body, a maximum height of the sheet body along the longitudinal axis of the sheet body ranges between 31.1 and 37.9 cm, the sheet body has a first extension portion, a second extension portion opposite to the first extension portion, a third extension portion and a fourth extension portion opposite to the third extension portion, a length from a free end of the first extension portion to a free end of the second extension portion along an axis perpendicular or substantially perpendicular to the longitudinal axis of the sheet body ranges between 50.0 and 58.2 cm, and a length from a free end of the third extension portion to a free end of the fourth extension portion along an axis perpendicular or substantially perpendicular to the longitudinal axis of the sheet body ranges between 44.3 and 52.1 cm.

In certain embodiments, the maximum height of the sheet body along the longitudinal axis of the sheet body ranges between 31.1 and 37.9 cm, the length from the free end of the first extension portion to the free end of the second extension portion along an axis perpendicular or substantially perpendicular to the longitudinal axis of the sheet body ranges between 43.0 and 50.0 cm, and the length from the free end of the third extension portion to the free end of the fourth extension portion along the axis perpendicular or substantially perpendicular to the longitudinal axis of the sheet body ranges between 37.7 and 44.3 cm.

In certain embodiments, the covering structure includes a longer adjusting strap and a shorter adjusting strap, a length of the longer adjusting strap is between 57.6 and 70.4 cm, and a length of the shorter adjusting strap is between 51.3 and 62.7 cm.

In certain embodiments, the control device includes a direct current (DC) power supply unit, a control unit and a pulse output circuit. The DC power supply unit can provide power for operation of the control device. The control unit can generate and transmit a plurality of control signals. The pulse output circuit is electrically connected to the control unit. The pulse output circuit can receive power from the DC power supply unit and the control signals from the control unit, form at least one current pulse signal having a predetermined waveform based on the characteristics of at least one of the control signals, and transmit the current pulse signal to the electrode pad unit.

This and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION

Figure 1:
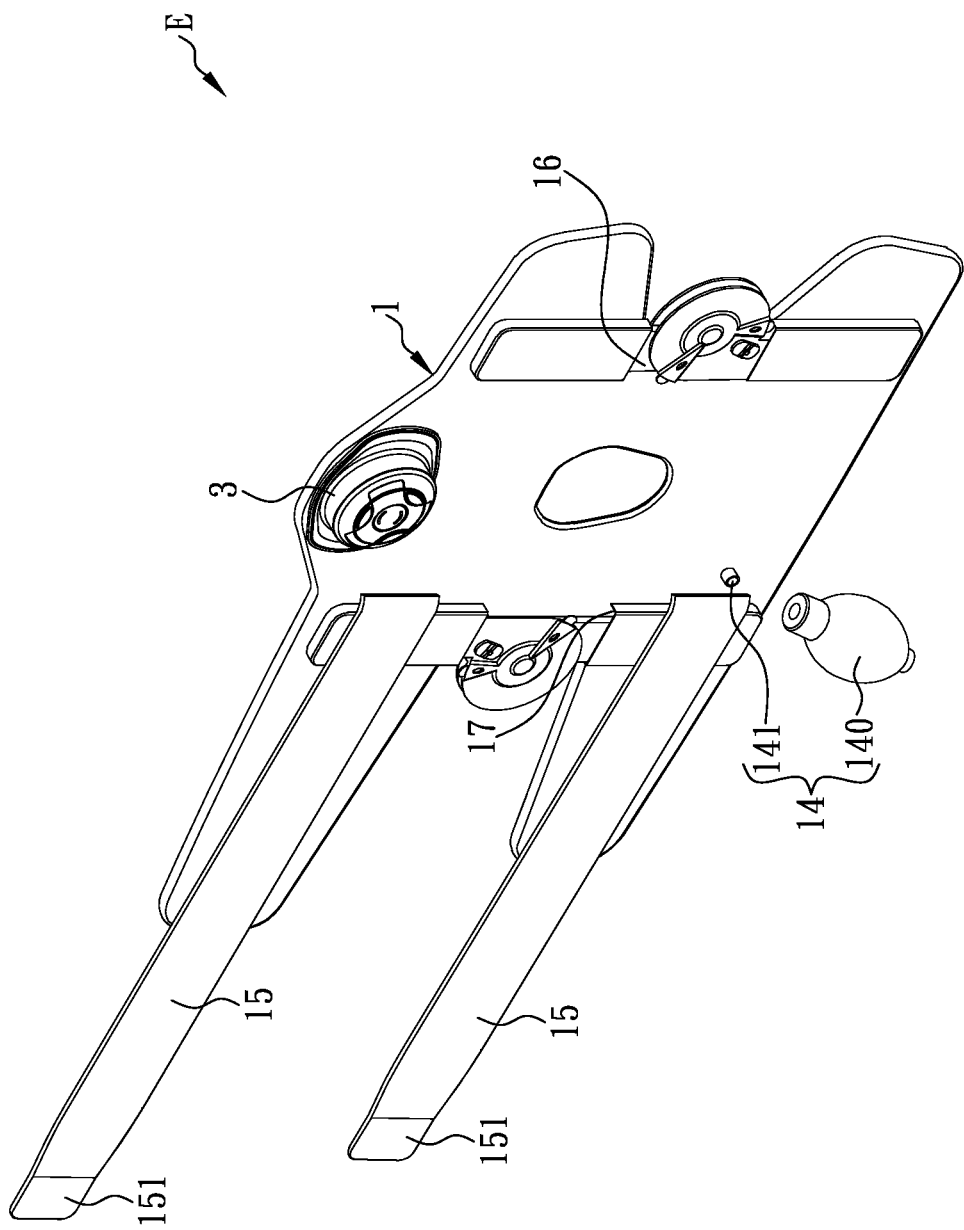
FIG. 1 is a perspective view of a body joint support device according to certain embodiments of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, parts or the like, which are for distinguishing one component/part from another one only, and are not intended to, nor should be construed to impose any substantive limitations on the components, parts or the like, or be relevant to the sequence in which the components/parts are to be assembled or disposed in practical application.

As used herein, the term "substantially" refers to, for example, a value, or an average of values, in an acceptable deviation range of a particular value recognized or decided by a person of ordinary skill in the art, taking into account any specific quantity of errors related to the measurement of the value that may resulted from limitations of a measurement system or device. For example, "substantially" may indicate that the value is within, for example, ±5%, ±3%, ±1%, ±0.5% or ±0.1%, or one or more standard deviations, of the particular value.

One aspect of the present disclosure is directed to a body joint support device E including a covering structure 1 and configured to abut against at least one body joint and accommodate in configuration both to the bending state and non-bending state of the at least one body joint. The covering structure 1 can to be fixed to a human joint through at least one adjusting strap 15 and/or through the elasticity of the covering structure 1. Since the covering structure 1 exerts a force on the body joint(s) applied, it can support and assist the body joint(s) to stably stay in a static position, for example, keep an elbow of a user in a stable bending position. Also, the covering structure 1 can support and assist the body joint(s) to be stably in an active position within a limited range. For example, the covering structure 1 can prevent a user from walking with feet splayed out. In addition, with the elasticity of the covering structure 1, when the user moves, such as walking, a restoring force would be exerted by the covering structure 1 to the body joint(s) to support and help the moving body joint(s) to recover to its natural and normal movement range. For example, the soles of the feet of a user bend when he or she is walking, and the bending drives the covering structure 1 to bend as well. At this time, the restoring force of the covering structure 1 drives the covering structure 1 to return to its non-bending configuration, and therefore support and help the soles to return to a substantially straight (substantially horizontal) state. As used herein, an inner surface of the covering structure 1 or of a covering body 11 refers to a surface that faces the skin of a body joint when the body joint support device E is applied to a body joint, and an outer surface of the covering structure 1 or the covering body 11 refers to a surface that faces away from the skin of a body joint when the body joint support device E is applied to the body joint.

Figure 2:
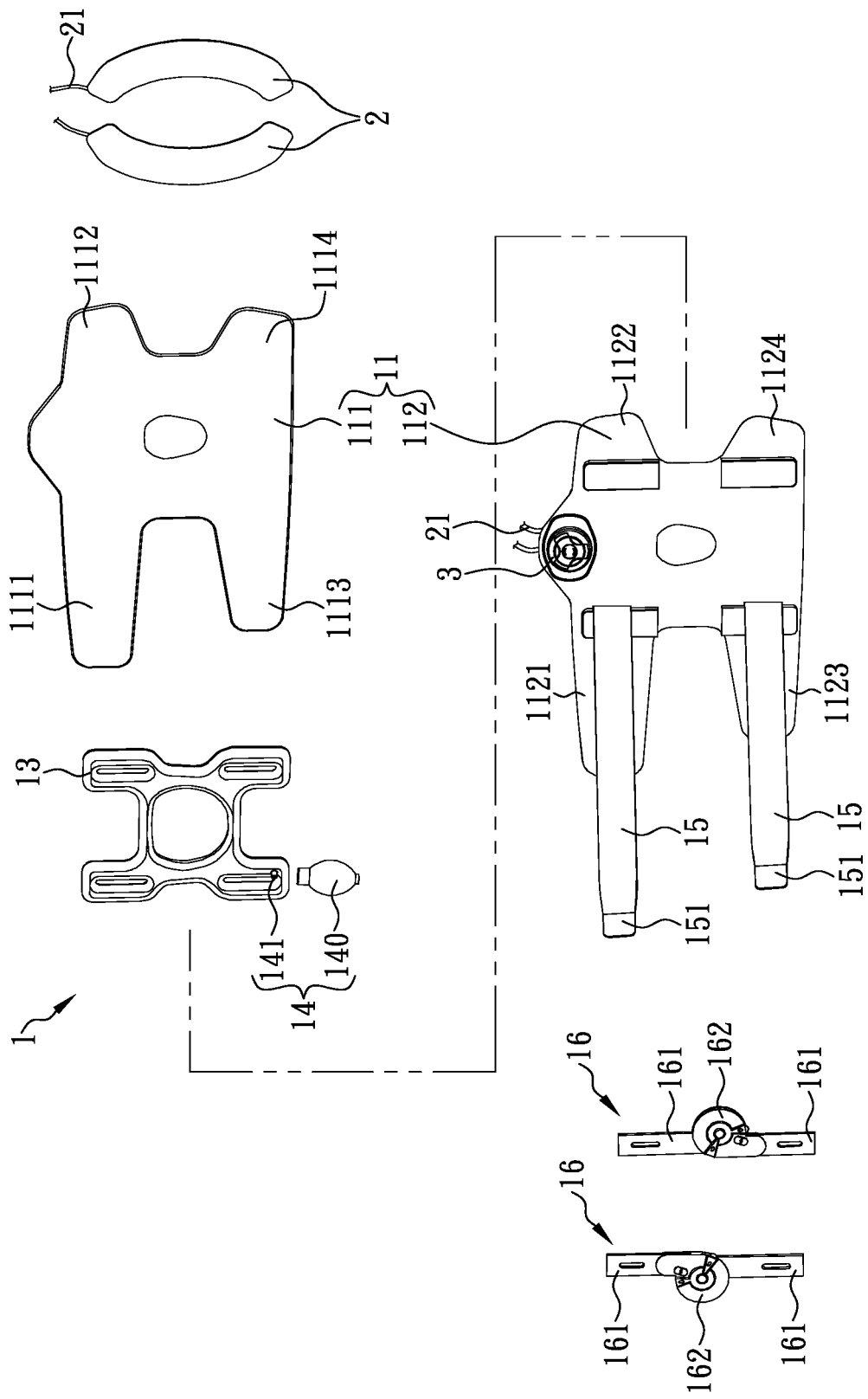
FIG. 2 is an exploded view of the body joint support device according to certain embodiments of the present disclosure.
Figure 3:
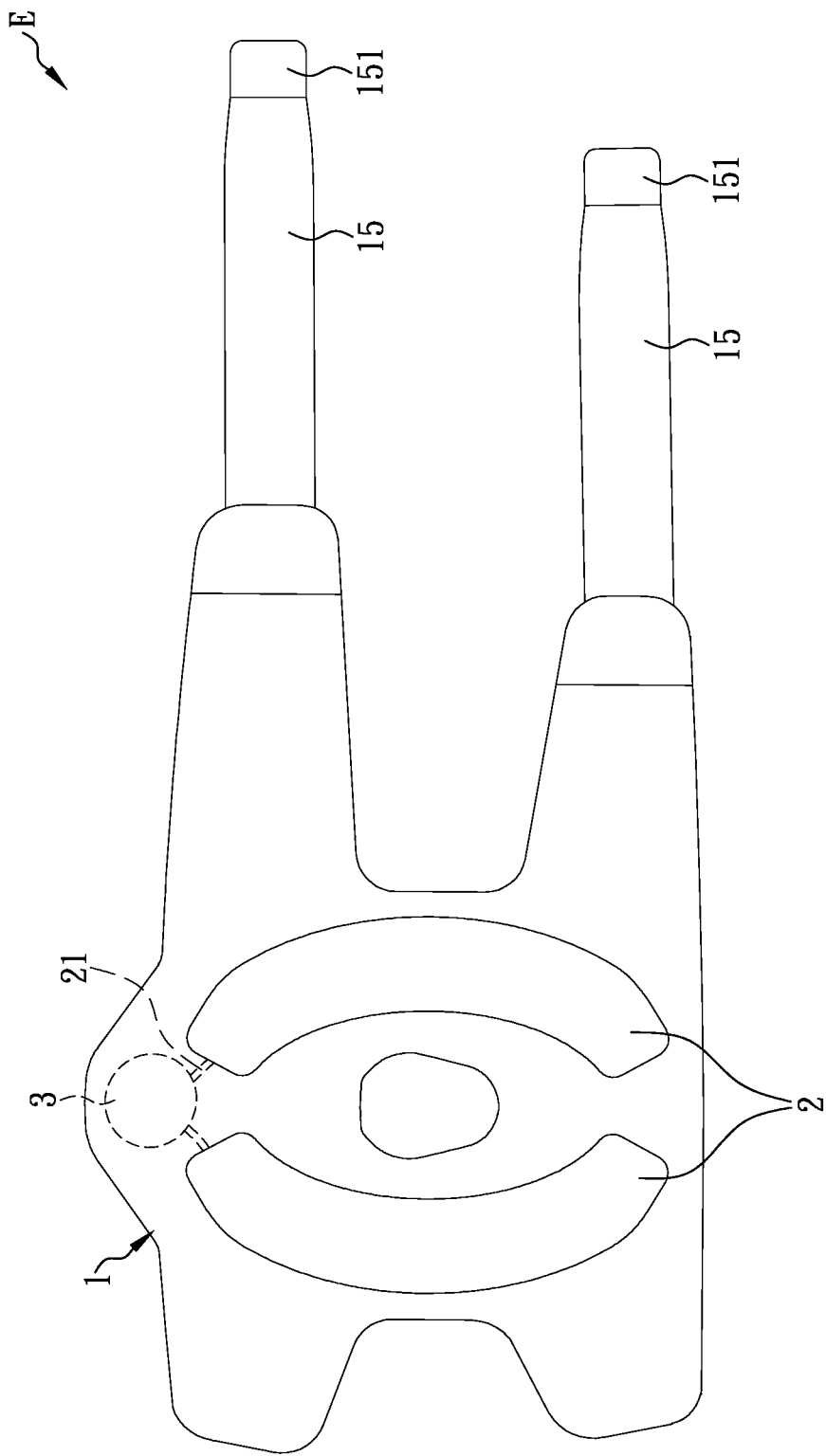
FIG. 3 is a rear view of the body joint support device according to certain embodiments of the present disclosure.

Referring to FIGS. 1-3, in certain embodiments, the body joint support device E includes the covering structure 1, at least one electrode pad unit 2 and a control device 3. The covering structure 1 is configured to be worn to and cover at least one body joint, such as waist, ankle, knee, elbow, shoulder, etc., and configured to press the surface of the skin of the body joint with the inner surface of the covering structure 1 through the force generated by the covering structure 1 itself.

Referring to FIG. 2, the covering structure 1 includes the covering body 11, at least one airbag 13, at least one inflating device 14 and at least one adjusting strap 15 (two adjusting straps 15 are exemplarily shown in FIG. 2). The covering body 11 includes a first sheet body 111 and a second sheet body 112. However, the present disclosure is not limited thereto. In certain embodiments, the airbag 13 may be omitted, and the body joint support device E presses tightly against the surface of the skin of the body joint with the inner surface of the covering structure 1 through the tension and pressing force generated by pulling tight the adjusting strap 15 and fixing the pulled adjusting strap 15 on the second sheet body 112. In certain embodiments, the covering body 11 can include only a single sheet body or three or more sheet bodies. As used herein, an inner surface of the first sheet body 111 or the second sheet body 112 refers to a surface that faces the other sheet body 112 or 111 when the two sheet bodies are assembled together, and an outer surface of the first sheet body 111 or the second sheet body 112 refers to a surface that faces away from the other sheet body 112 or 111 when the two sheet bodies are assembled together.

The covering body 11 is flexible or elastic, and is configured to be bent to cover and/or wrap around at least one body joint, for example, a knee of a user. The outer surface of the first sheet body 111 can serve as the inner surface of the covering body 11, and in certain embodiments the first sheet body 111 can include, be made of, or be covered with a first material such as fabric or texture so as to afford more comfort to the skin when the covering body 11 is pressed against the skin. The outer surface of the second sheet body 112 can serve as the outer surface of the covering body 11, and the second sheet body 112 can be made of a second material having a hardness degree higher than the first material to provide higher structural strength than the first sheet body 111 does, such as plastic material. In certain embodiments, according to practical product requirements, at least one component or layer, for example, a waterproof layer, can be further arranged on the outer surface of the second sheet body 112 that serves as the outer surface of the covering body 11. The whole periphery or a portion of the periphery of the first sheet body 111 can be sealedly connected to or integrated with the corresponding whole periphery or a corresponding portion of the periphery of the second sheet body 112 by adhesive or other fixation means. A portion of the first sheet body 111 that is not sealedly connected to or integrated with the second sheet body 112 and a portion of the second sheet body 112 that is not sealedly connected to or integrated with the first sheet body 111 collectively defines an accommodating space for accommodating components required by the body joint support device E.

Referring to FIGS. 1-3, in certain embodiments, the airbag 13 can be located between the first sheet body 111 and the second sheet body 112, that is, located in the covering body 11 and in the accommodating space. The airbag is configured to expand, when inflated, along a direction toward the inner surface of the covering body 11. For example, when the covering body 11 is wrapped around a knee of the user, and the airbag 13 expands along the direction toward the inner surface of the covering body 11, the force applied by the airbag 13 presses the first sheet body 111 and the inner surface of the covering body 11 toward the skin of the knee, so that the first sheet body 111 is pressed against the skin of the knee. Further, the inflating device 14 is configured to be connected to the airbag 13.

Referring to FIGS. 1, 2, 5 and 6, in certain embodiments, the inflating device 14 includes an inflating member 140 and an air valve 141 configured to communicate with the airbag 13 and to be fixed on the covering structure 1. The inflating member 140 can be a hand press inflation pump. However, the present disclosure is not limited thereto. In certain embodiments, the inflating member 140 can be an electric inflation pump. The inflating member 140 is configured to be directly connected to the air valve 141 so that the inflating member 140 can inflate or deflate the airbag 13 to change the expansion degree or deflation degree of the airbag 13. In certain embodiments, the air valve 141 is provided therein with a spring and with a spring-driven open/close mechanism, and is configured to open when the inflating member 140 is attached to the air valve 141 and the spring in the air valve 141 is pressed by the inflating member 140, so as to allow the airbag 13 to be inflated by the inflating member 140, and configured to close when the inflating member 140 is detached from the air valve 141 and the spring is released and returns to its uncompressed state, which therefore locks and closes the air valve 141. However, the present disclosure is not limited thereto. In certain embodiments, the inflating device 14 may further include at least one pipe body. One end of the pipe body can be connected to the air valve 141 or penetrate the second sheet body 112 and be connected to the airbag 13, and the other end of the pipe body can be connected to the inflating member 140, so that the inflating member 140 can inflate or deflate the airbag 13 to change the expansion degree or deflation degree of the airbag 13. After the inflation is completed, the pipe body can be removed from the air valve 141, that is, only the air valve 141 and not the pipe body is retained on the covering structure 1, so that the user would not be interfered by the pipe body or the inflating member 140 during his or her movement.

Referring again to FIG. 6, in certain embodiments, the inflating device 14 may further include a switch member 144 for switching an air valve 141 between open and closed states that does not have the spring-controlled mechanism for opening or closing the air valve 141 as described supra or, for the air valve 141 having the spring-controlled open/close mechanism, to overwrite the spring-controlled open/close mechanism. The switch member 144 is configured to control and switch the air valve 141 between the open state and the closed state. In certain embodiments, when the air valve 141 is provided with the spring-controlled open/close mechanism, the switch member 144 is configured to be switched to press the spring to allow the air valve 141 to open even when the inflating member 140 or one end of the pipe body is not attached to the air valve 141, or block the pressing on the spring from, and therefore protecting the spring from being pressed by, the inflating member 140 or one end of the pipe body to allow the air valve 141 to close even when the inflating member 140 or one end of the pipe body is attached to the air valve 141. When the inflating member 140 or one end of the pipe body is connected to the air valve 141, and the air valve 141 is in the open state either because of the connection or attachment of the inflating member 140 or the pipe body to the air valve 141 or being controlled by the switch member 144, the inflating device 140 can inflate the airbag 13. Then, a user can operate the switch member 144 to switch, or can remove the inflating member 140 or the pipe body to return, the air valve 141 to the closed state, so that the air in the airbag 13 cannot flow out through the air valve 141. In certain embodiments, the air valve 141 and the switch member 144 can be integrated into a Schrader valve or American valve to reduce the overall weight of the body joint support device E.

Referring again to FIGS. 1 and 2, one end of each of the adjusting straps 15 is connected to the outer surface of the second sheet body 112 that serves as the outer surface of the covering body 11, and the other end of each of the adjusting straps 15 is provided with a fixing portion 151. The fixing portion 151 is configured to be fixed to the outer surface of the second sheet body 112 that serves as the outer surface of the covering body 11. When an adjusting strap 15 is pulled tight and fixed to the outer surface of the covering body 11, the adjusting strap 15 presses the inner surface of the covering body 11 so that the inner surface of the covering body 11 abuts against the skin of a body joint such as a knee. In certain embodiments, the fixing portion 151 can be at least one component that has fixing property, such as at least one hook-and-loop fastener, button, hook, etc., and a fixing structure corresponding to and configured to be fixed with the fixing portion 151 is provided on the outer surface of the covering body 11, so that the fixing portion 151 can be fixed to the outer surface of the covering body 11 by the fixing structure.

Referring again to FIGS. 2 and 3, in certain embodiments, the covering structure 1 includes at least two adjusting straps 15. The length of one of the two adjusting straps 15 is smaller than the length of the other one of the two adjusting straps 15. In certain embodiments, a first length from the end of a longer adjusting strap 15 that is connected to the outer surface of the second sheet body 112 to the free end of the fixing portion 151 of the longer adjusting strap 15 is between 57.6 and 70.4 cm, and more preferably, between 62.7 and 65.3 cm, while a second length from the end of a shorter adjusting strap 15 that is connected to the outer surface of the second sheet body 112 to the free end of the fixing portion 151 of the shorter adjusting strap 15 is between 51.3 and 62.7 cm, and more preferably, between 55.9 and 58.1 cm.

Referring again to FIGS. 2 and 3, in certain embodiments, each of the first sheet body 111 and the second sheet body 112 has a maximum height along the longitudinal axis thereof that ranges between 31.1 and 37.9 cm, and more preferably between 33.8 and 35.2 cm. The second sheet body 112 has a first extension portion 1121, a second extension portion 1122, a third extension portion 1123 and a fourth extension portion 1124. The first extension portion 1121 is located opposite to the second extension portion 1122, and the third extension portion 1123 is located opposite to the fourth extension portion 1124. The end of the longer adjusting strap 15 that is connected to the second sheet body 112 corresponds to the first extension portion 1121, and the end of the shorter adjusting strap 15 that is connected to the second sheet body 112 corresponds to the third extension portion 1123. In certain embodiments, a third length from a free end of the first extension portion 1121 to a free end of the second extension portion 1122 along an axis perpendicular or substantially perpendicular to the longitudinal axis of the second sheet body 112 ranges between 50.0 and 58.2 cm, and more preferably between 53.0 and 55.2 cm, while a fourth length from a free end of the third extension portion 1123 to a free end of the fourth extension portion 1124 along an axis perpendicular or substantially perpendicular to the longitudinal axis of the second sheet body 112 ranges between 44.3 and 52.1 cm, and more preferably between 47.2 and 49.2 cm. In certain embodiments, the third length ranges between 43.0 and 50.0 cm, and more preferably between 45.6 and 47.4 cm, while the fourth length ranges between 37.7 and 44.3 cm, and more preferably between 40.2 and 41.8 cm.

Referring again to FIG. 2, The first sheet body 111 has a fifth extension portion 1111, a sixth extension portion 1112, a seventh extension portion 1113 and an eighth extension portion 1114. The fifth extension portion 1111, sixth extension portion 1112, seventh extension portion 1113 and eighth extension portion 1114 correspond to the first extension portion 1121, second extension portion 1122, third extension portion 1123 and fourth extension portion 1124, respectively. The fifth extension portion 1111 is located opposite to the sixth extension portion 1112, and the seventh extension portion 1113 is located opposite to the eighth extension portion 1114. In certain embodiments, a fifth length from a free end of the fifth extension portion 1111 to a free end of the sixth extension portion 1112 along an axis perpendicular or substantially perpendicular to the longitudinal axis of the first sheet body 111 ranges between 50.0 and 58.2 cm, and more preferably between 53.0 and 55.2 cm, while a sixth length from a free end of the seventh extension portion 1113 to a free end of the eighth extension portion 1114 along an axis perpendicular or substantially perpendicular to the longitudinal axis of the first sheet body 111 ranges between 44.3 and 52.1 cm, and more preferably between 47.2 and 49.2 cm. In certain embodiments, the fifth length ranges between 43.0 and 50.0 cm, and more preferably between 45.6 and 47.4 cm, while the sixth length ranges between 37.7 and 44.3 cm, and more preferably between 40.2 and 41.8 cm.

Referring again to FIGS. 2 and 3, at least one electrode pad unit 2 can be disposed on the outer surface of the first sheet body 111, that is, the inner surface of the covering structure 1. Each electrode pad unit 2 can include conductive material such as conductive fiber, conductive film, conductive fabric, etc., and in certain embodiments, can be electrically connected to the control device 3 through a corresponding conductive wire 21. The control device 3 can be configured as a transcutaneous electrical nerve stimulator (TENS), an electrical muscle stimulation (EMS) device, etc., and each electrode pad unit 2 can receive the electrical stimulation signal from the control device 3, and output the electrical stimulation to a body joint wrapped by the covering structure 1, such as a knee of a user, so as to achieve the effects of electrotherapy and/or heat therapy.

Figure 4:
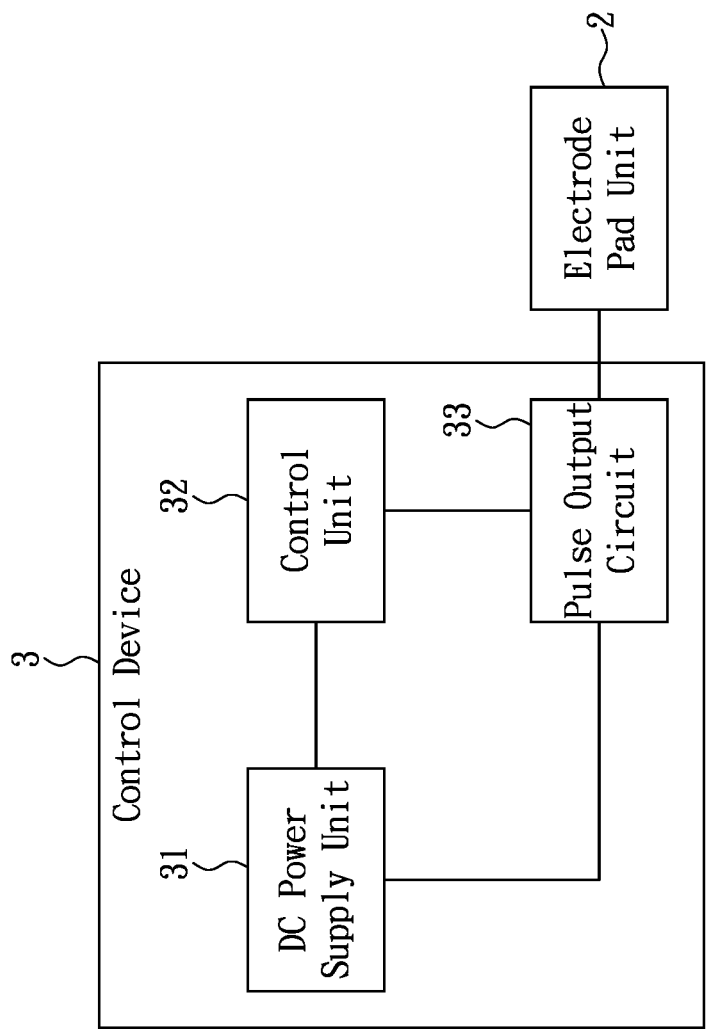
FIG. 4 is a block diagram of a control device according to certain embodiments of the present disclosure.

Referring to FIG. 4, the control device 3 can be fixed to the outer surface of the second sheet body 112, that is, the outer surface of the covering body 11. The control device 3 includes a DC power supply unit 31 such as at least one dry battery, a control unit 32, and a pulse output circuit 33. The DC power supply unit 31 is configured to provide the power required for the operation of the control device 3. The control unit 32 is configured to generate and transmit a plurality of control signals to the pulse output circuit 33. The pulse output circuit 33 is configured to receive power from the DC power supply unit 31 and the control signals from the control unit 32, form at least one current pulse signal having a predetermined waveform based on the characteristics of at least one of the control signals, and transmit the current pulse signal to the electrode pad unit 2 via the conductive wire 21. The electrode pad unit 2 is configured to receive the current pulse signal and output current corresponding to the current pulse signal to stimulate, and/or output current to heat, the muscles of the body part(s) where the body joint support device E is wrapped on. At least one button may be arranged on the control device 3, so that a user can operate on the button to enable the control device 3 to start outputting and/or stop outputting electrical pulses, and/or outputting electrical pulses of different magnitudes and/or frequencies. In certain embodiments, the control device 3 is configured to receive wireless signals, such as Bluetooth and/or WiFi signals, so that a user can operate on a wireless controller to control the control device 3 to start outputting and/or stop outputting electrical pulses, and/or outputting electrical pulses of different magnitudes and/or frequencies.

Figure 5:
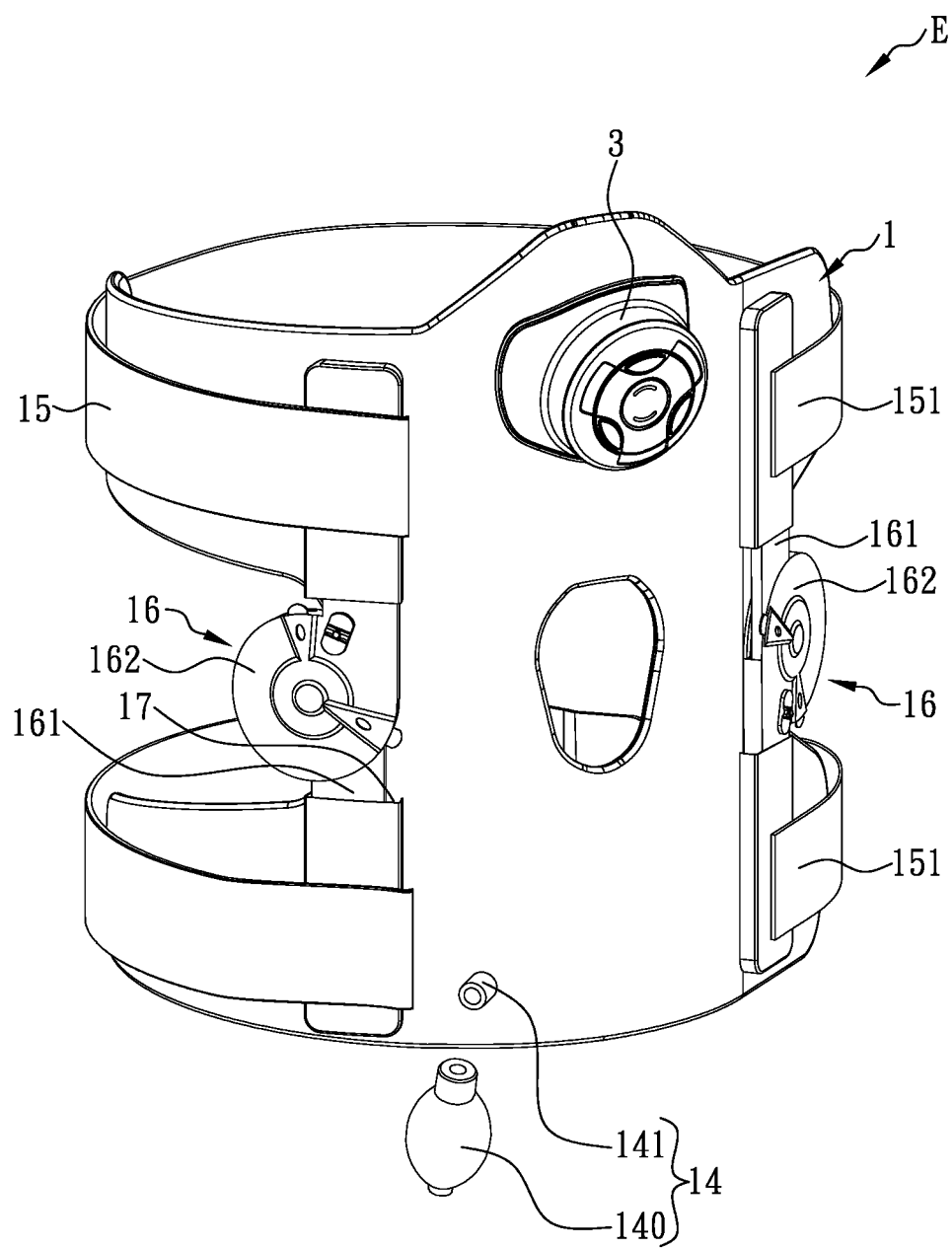
FIG. 5 is a perspective view of the body joint support device being curved according to certain embodiments of the present disclosure.

Referring to FIG. 5, when a user bends the covering structure 1 to wrap the covering structure 1 around at least one body joint, for example, one of his or her knees, the upper portion of the covering structure 1 covers an area of the thigh of the user that is connected to and adjacent to the knee, the middle portion of the covering structure 1 covers the knee, and the lower portion of the covering structure 1 covers an area of the calf of the user that is connected to and adjacent to the knee. Then, the user can pull the adjusting strap(s) 15 to press the inner surface of the covering structure 1 as well as the electrode pad unit(s) 2 disposed thereon so that the inner surface of the covering structure 1 and the electrode pad unit(s) 2 abut against the skin at the aforementioned thigh, knee and calf areas. The rear side of the upper portion and the rear side of the lower portion of the covering structure 1 can bend close to each other when the knee is in movement. In certain embodiments, the covering structure 1 further includes at least one angle adjustable support member 16. The angle adjustable support member 16 may be made of metal, for example, aluminum, titanium, stainless steel, etc., carbon fiber, or other material that has high stiffness and/or high tensile strength, and is configured to provide support through its stiffness and/or tensile strength and adjustable fixed configuration to the body joint to which the covering structure 1 is wrapped. The angle adjustable support member 16 includes at least two plate bodies 161 configured to be fixed and locked at a particular angle relative to each other that is adjustable by a user through an angle adjustment member 162. One end of each of the plate bodies 161 is engaged with the angle adjustment member 162, and the angle adjustment member 162 is configured to hinge the engaged end of one plate body 161 to the engaged end of the other plate body 161 and fix the plate bodies 161 at a particular angle relative to each other that is chosen by the user. The angle adjustment member 162 includes an angle scale member configured to be operated by a user to adjust, and indicate, the angle between the plate bodies 161, so that the user may choose an angle he or she deems appropriate, for example, an angle that allows the plate bodies 161 to support the body joint without impeding the movement of the body joint, and a locking member configured to lock and fix the plate bodies 161 at the particular angle relative to each other that is chosen by the user. An end of each plate body 161 that is opposite to the end engaged with the angle adjustment member 162, that is, each of both ends of the angle adjustable support member 16, can be inserted into a corresponding slot 17 formed on the outer surface of the covering body 11, and the movement of this opposite end is limited by the slot 17, so that the structural support for the body joint by the angle adjustable support member 16 can be effected. In certain embodiments, the slot 17 may be formed by a cover structure that is attached or integratedly formed on the outer surface of the covering body 11 and is formed with an accommodating room therebetween for accommodating the opposite end of the plate body 161. In certain embodiments, the end of an adjusting strap 15 that is connected to the outer surface of the second sheet body 112 may be fixed to the cover structure, and the cover structure may be made of fabric, plastic, or other material whose structural integrity or strength can withstand constant pulling force from a user. In certain embodiments, the opposite end can be formed with a through hole thereon so as to reduce the weight of the plate body 161 and/or be engaged with an engaging structure formed in the slot 17 to provide further strength for the fixation between the opposite end and the corresponding slot 17.

After finishing pulling the adjusting strap 15, a user can operate the inflating device 14 to inflate the airbag 13 to press the electrode pad unit 2 so that the electrode pad unit 2 tightly abuts against the skin surface through the expansion of the airbag 13 within the extent that the user does not feel uncomfortable. When the user walks or runs with the body joint support device E being worn at a body joint such as his or her knee, the covering body 11 bends and the airbag deforms with knee movement. As the air charged into the airbag 13 is not discharged from and remains in the airbag 13, the air continuously exerts pressure to the first sheet body 111 through the airbag 13 and therefore presses the first sheet body 111 and the electrode pad unit 2 thereon so that the first sheet body 111 and the electrode pad unit 2 tightly abut against the skin of the knee wrapped with the body joint support device E. Therefore, the electrode pad unit 2 does not come off from the knee as a result of frequent knee movement. Further, with the expansion of the airbag 13, the covering structure 1 can also achieve an effect of reducing the fluid accumulated around the body joint through compression, and the effects of compression therapy, as compression therapy ordinarily applies pressure to an affected area (such as the legs) to slowly stretch the vein walls at the area to improve blood circulation. Therefore, the user can adjust the expansion degree of the airbag 13 to change the pressure applied by the covering structure 1 to the skin according to the extent of the severity of his or her blood flow constriction.

Figure 6:
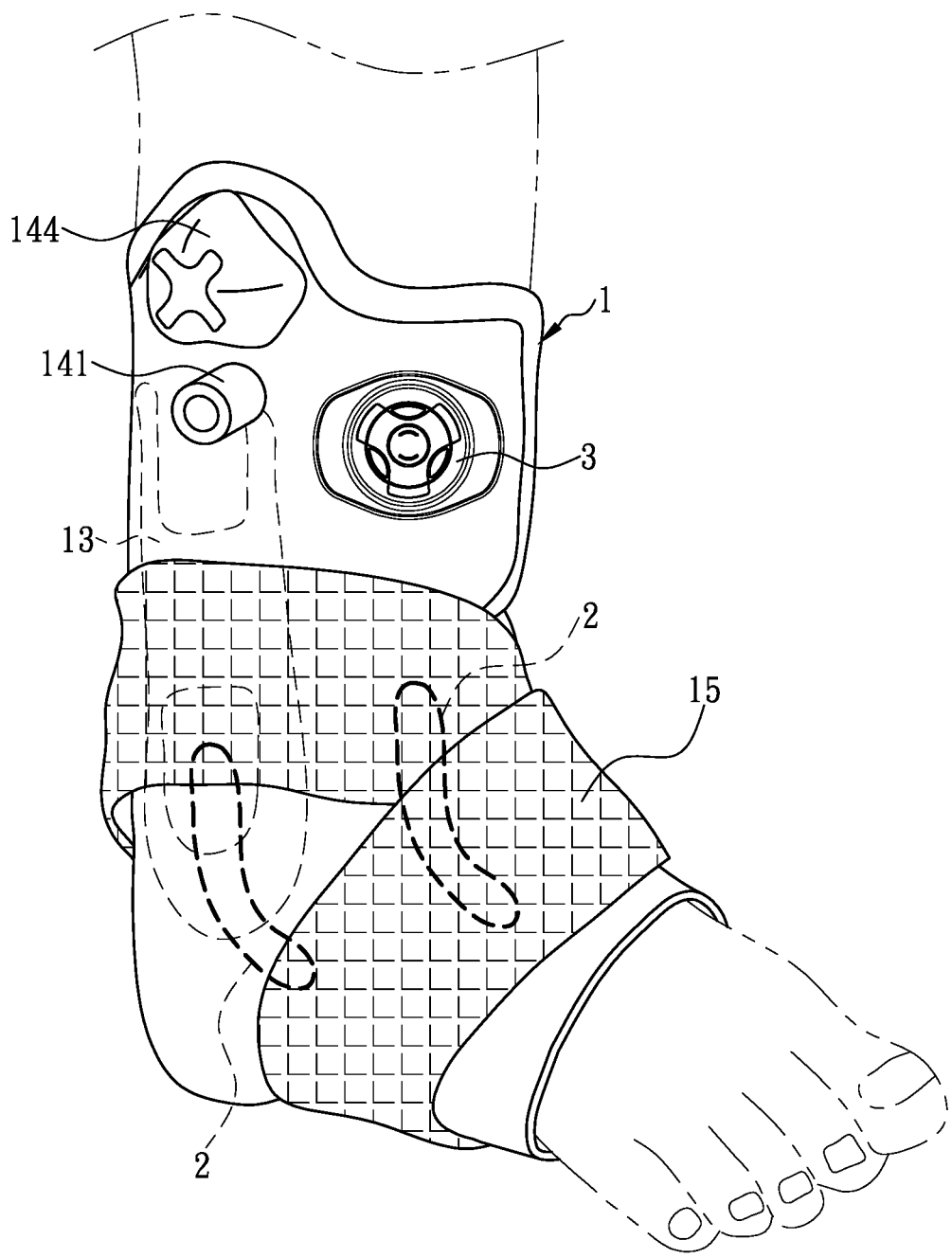
FIG. 6 is a perspective view of a body joint support device according to certain other embodiments of the present disclosure.

Referring to FIG. 6, in certain embodiments, the configuration and shape of the covering structure 1 may vary according to the contour of a body joint. For example, if a body joint needing care is an ankle, the covering structure 1 can cover the ankle joint, as well as part of the calf and part of the sole that are adjacent to the ankle joint. The inner surface of the covering structure 1 can be provided with two electrode pad units 2, one of the electrode pad units 2 corresponding to the medial malleolus region, and the other electrode pad unit 2 corresponding to the lateral malleolus region. However, the present disclosure is not limited thereto. The position of each electrode pad unit 2 can be changed according to product requirements and is not limited to the position shown in FIG. 6. The control device 3 can be fixed on the covering structure 1 and can transmit electrical stimulation signal to each of the electrode pad units 2. When the covering structure 1 covers the ankle, the control device 3 is located at the outer side of the calf. For example, as shown in FIG. 6, the control device 3 is located on the outer side of the right calf, that is, the right side of the right calf. In this way, when the user is walking, the control device 3 can be prevented from the touch or hit by the left calf, so as to avoid the button(s) on the control device 3 from being pressed by mistake, and avoid discomfort that can otherwise arise during walking. However, the present disclosure is not limited thereto.

Referring again to FIG. 6, the airbag 13 can be arranged in the covering structure 1 without being exposed therefrom. While only one airbag 13 is exemplarily shown in FIG. 6 for brevity, more preferably, the covering structure 1 can be provided with two airbags 13 corresponding to the positions of the electrode pad units 2 for the medial malleolus and lateral malleolus regions, respectively, so that when the airbags 13 are inflated and expanded, the airbags 13 force the electrode pad units 2 to tightly abut against the skin surface to maintain fine electrotherapy and heat therapy effects. In addition, after the covering structure 1 has covered the ankle, an adjusting strap 15 can be wound to the outer surface of the covering structure 1 to fix the covering structure 1. The adjusting strap 15 can be wrapped around the ankle joint first, and then be wrapped along a direction from instep toward the sole without covering the heel, so as to provide better ankle stability. However, the present disclosure is not limited to the aforementioned wrapping method, and as long as the adjusting strap 15 is wrapped to the covering structure 1 in a way that the covering structure 1 can be stabilized on the ankle without being detached therefrom due to the movement of the user, such a way is within the scope of the present disclosure. Further, depending on user needs, if the covering structure 1 needs to keep a body joint within a limited range of a specific body joint configuration, for example, to keep an injured joint in a limited range of a curved or straight shape, the covering structure 1 can also be provided therein with at least one metal or semi rigid rod body, so that after the covering structure 1 covers the body joint, the body joint can be stably maintained in the specific limited range of a configuration needed.

Figure 7:
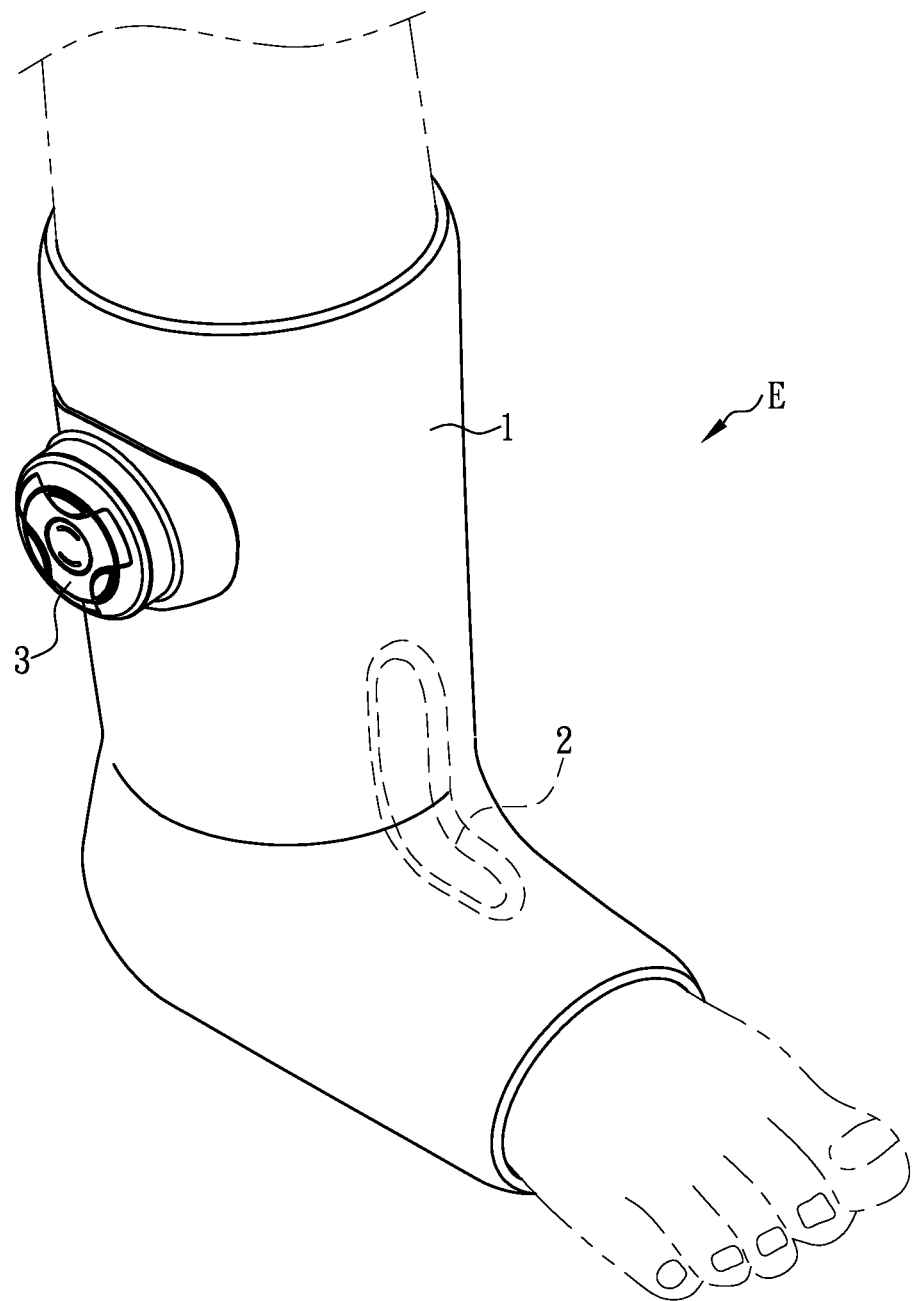
FIG. 7 is a perspective view of a body joint support device for an ankle according to certain embodiments of the present disclosure.
Figure 8:
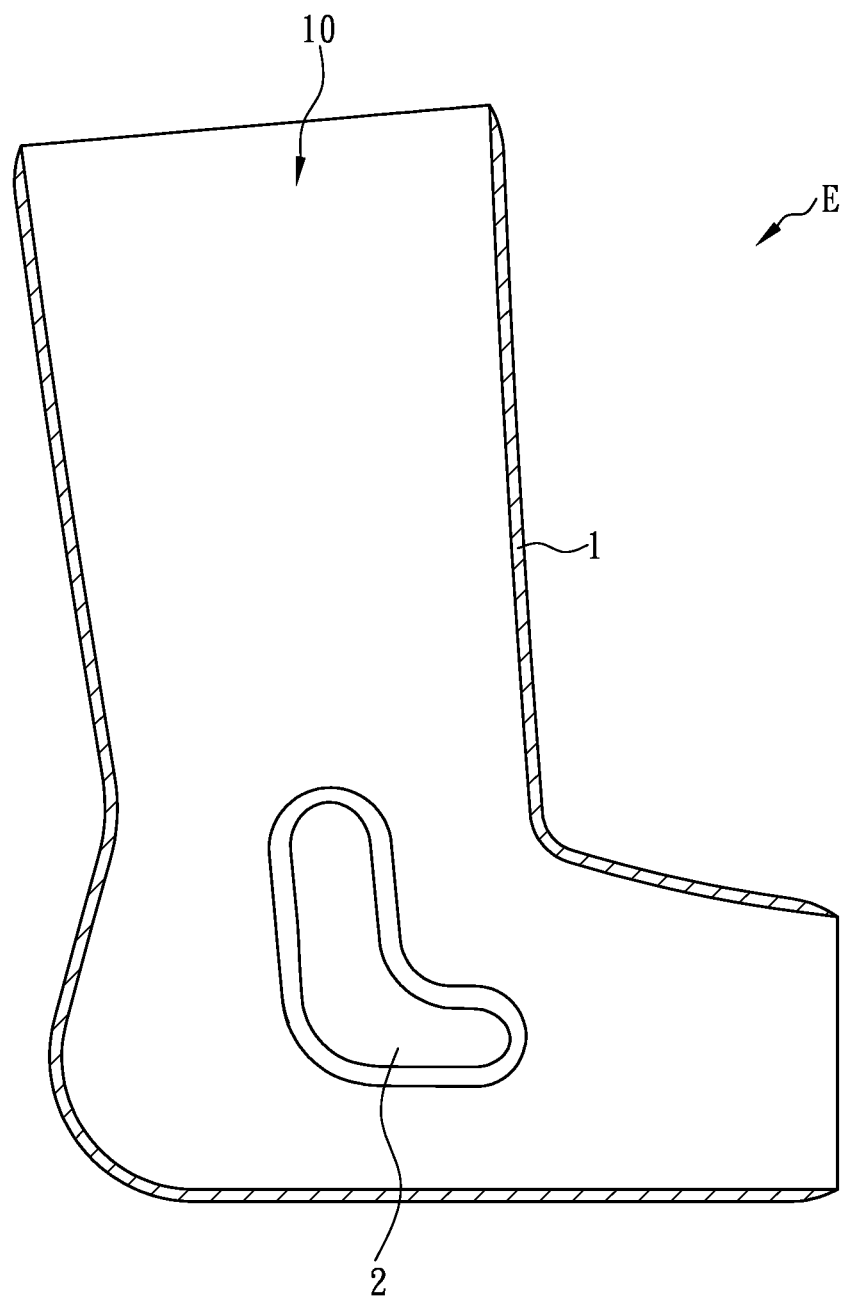
FIG. 8 is a cross-sectional view of the body joint support device shown in FIG. 7.

Referring to FIGS. 7 and 8, in certain embodiments, the covering structure 1 can include at least one elastic material such as nylon and latex wire, etc., and can be in a cylindrical shape to form a sleeving space 10 therein. The cylindrical covering structure 1 can be sleeved and fitted on a body joint such as an ankle. The electrode pad unit(s) 2 can be arranged on the inner surface of the cylindrical covering structure 1, and the control device 3 can be fixed to the outer surface of the cylindrical covering structure 1. The diameter of the sleeving space 10 under a non-stretching state that is formed in the cylindrical covering structure 1 is smaller than the diameter of a body joint to be applied with the body joint support device E. and therefore when the body joint support device E is worn on the body joint such as the ankle, the covering structure 1 is stretched and expanded by the body joint, and the restoring force produced by its own elasticity presses the inner surface of the covering structure 1 against the skin surface at the body joint. Therefore, the covering structure 1 can not only deform to adapt to the bending of the ankle, but also force the electrode pad unit(s) 2 to tightly abut against the skin surface.

Figure 9:
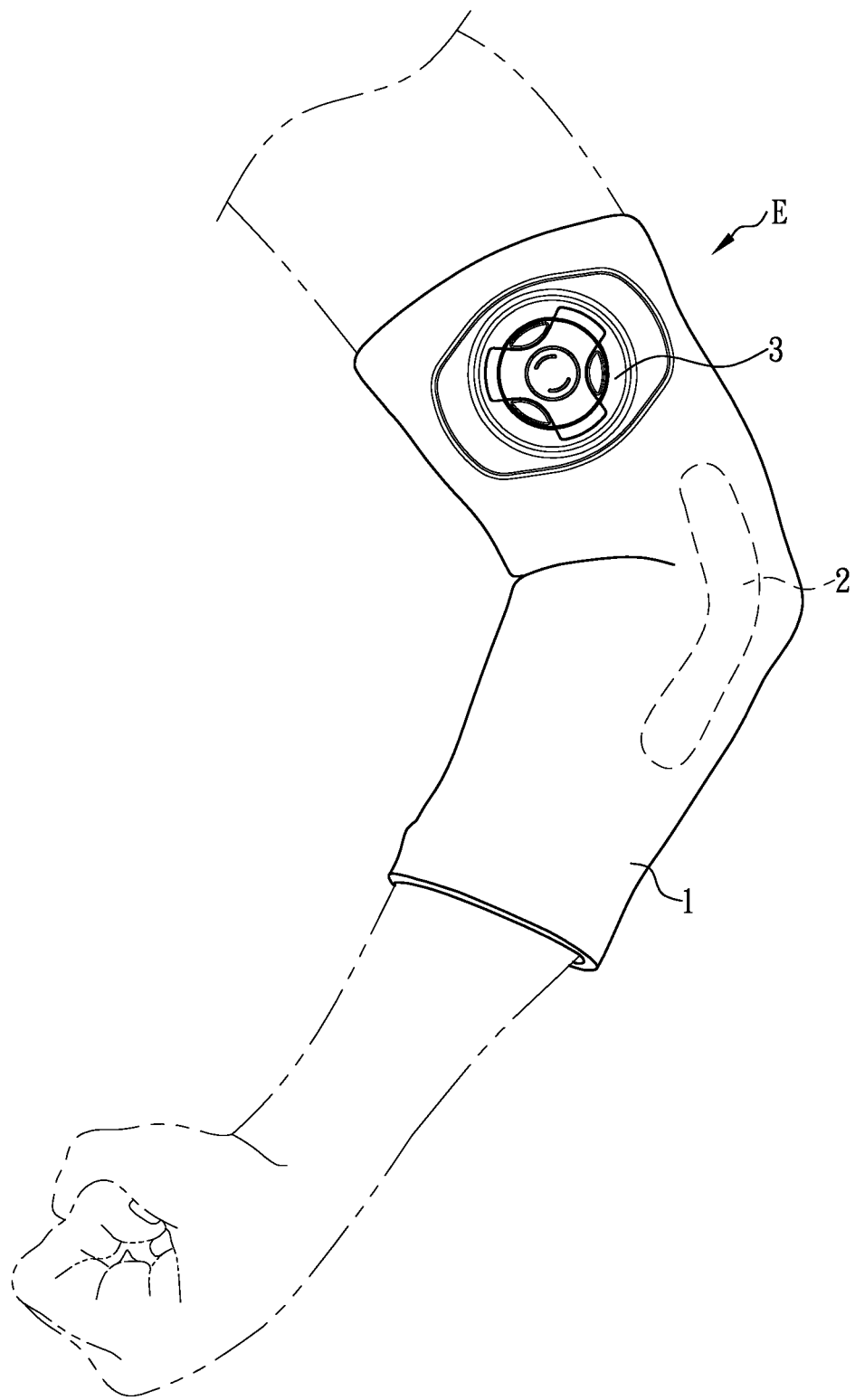
FIG. 9 is a perspective view of a body joint support device for an elbow joint according to certain embodiments of the present disclosure.
Figure 10:
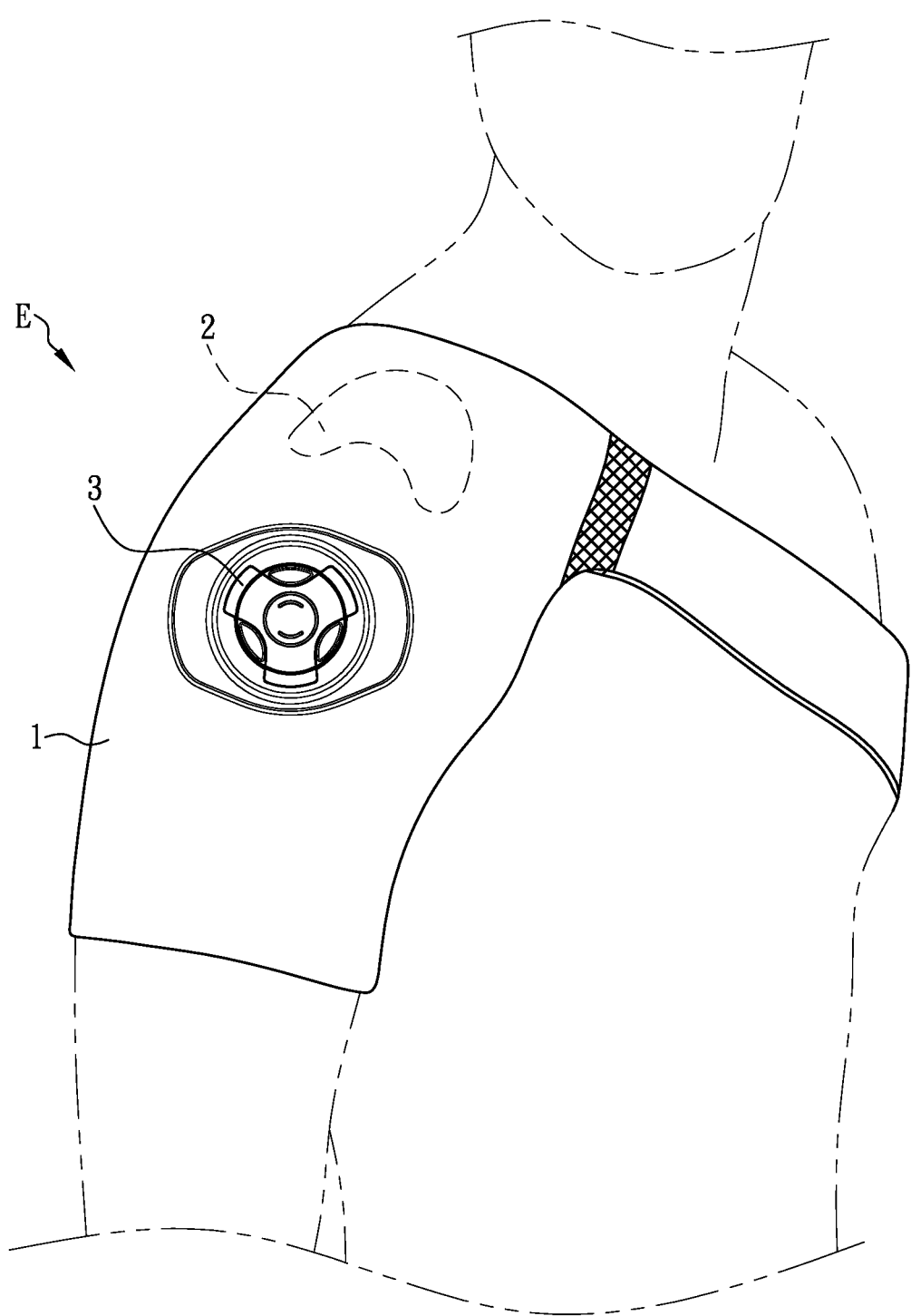
FIG. 10 is a perspective view of a body joint support device for a shoulder joint according to certain embodiments of the present disclosure.
Figure 11:
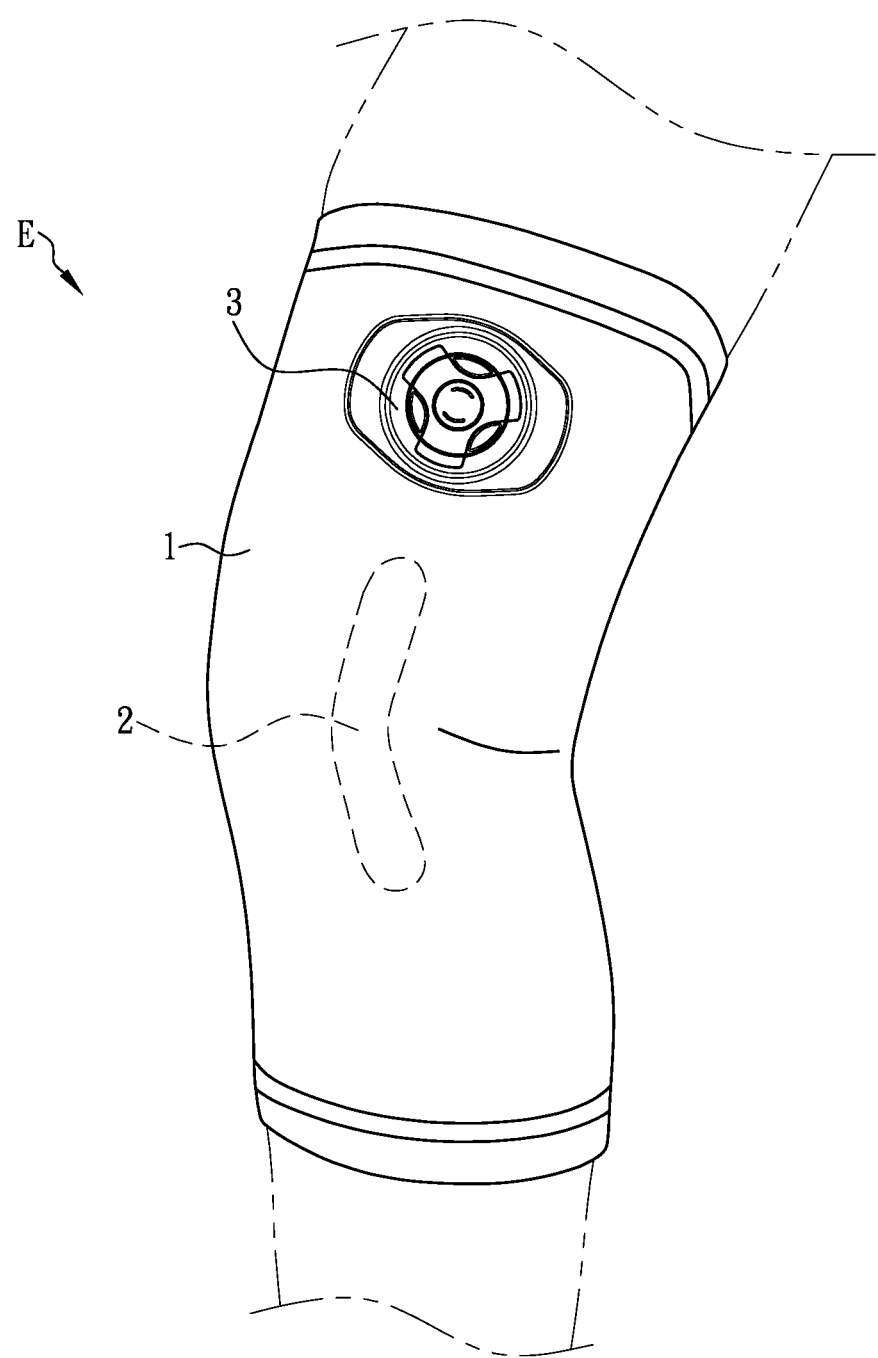
FIG. 11 is a perspective view of a body joint support device for a knee joint according to certain embodiments of the present disclosure.
Figure 12:
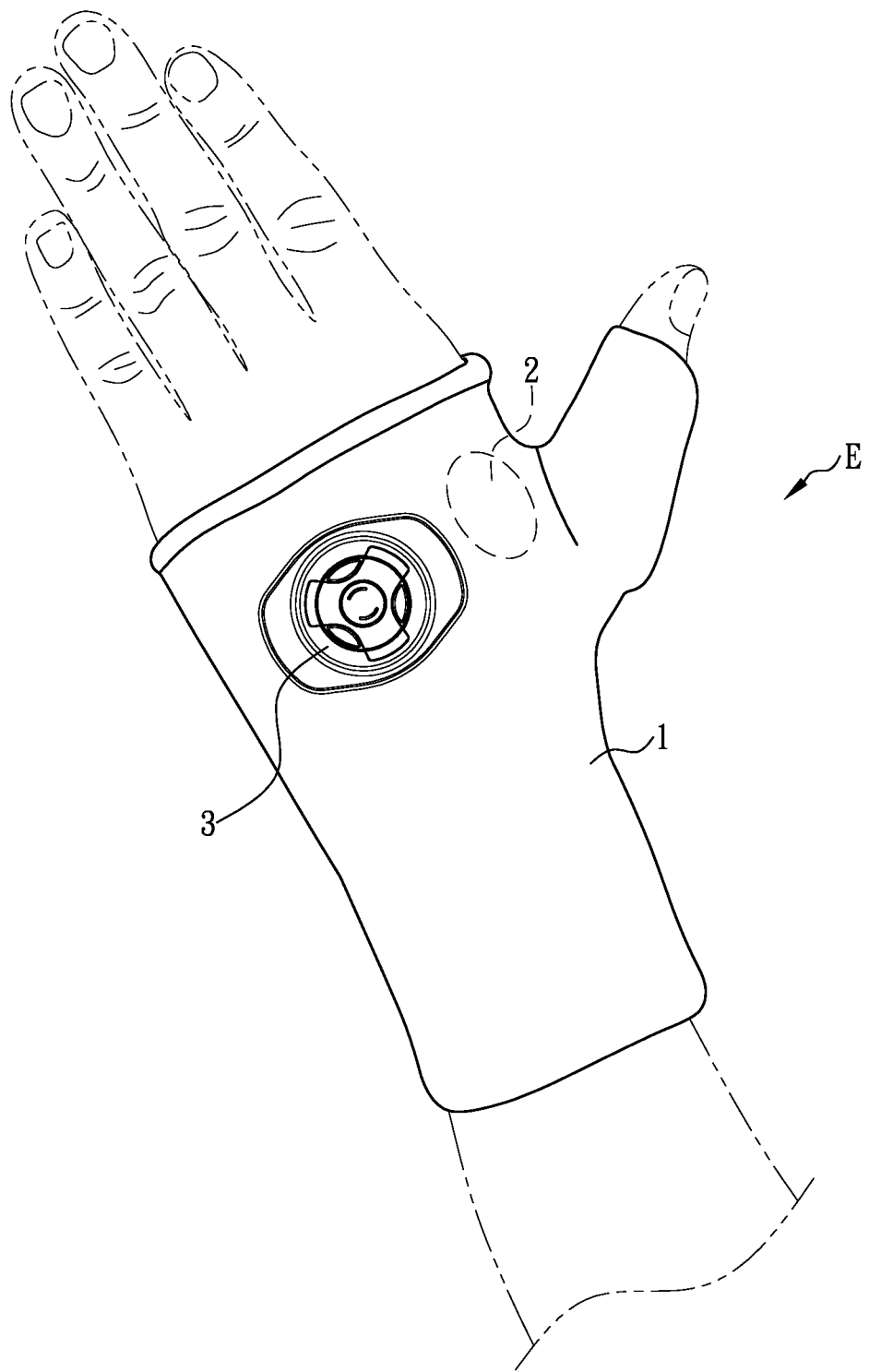
FIG. 12 is a perspective view of a body joint support device for a wrist joint according to certain embodiments of the present disclosure.
Figure 13:
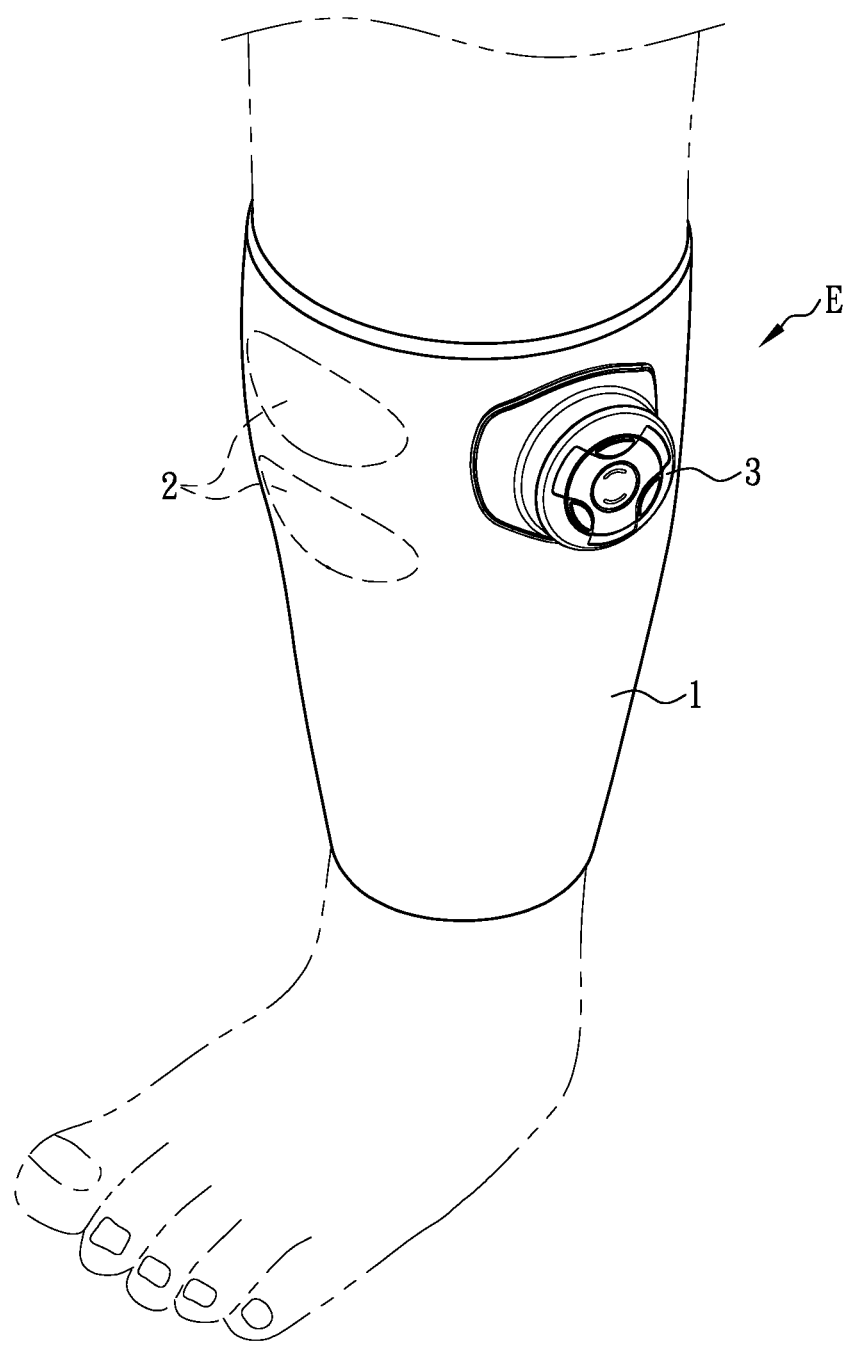
FIG. 13 is a perspective view of a body joint support device for the calve of a user according to certain embodiments of the present disclosure.
Figure 14:
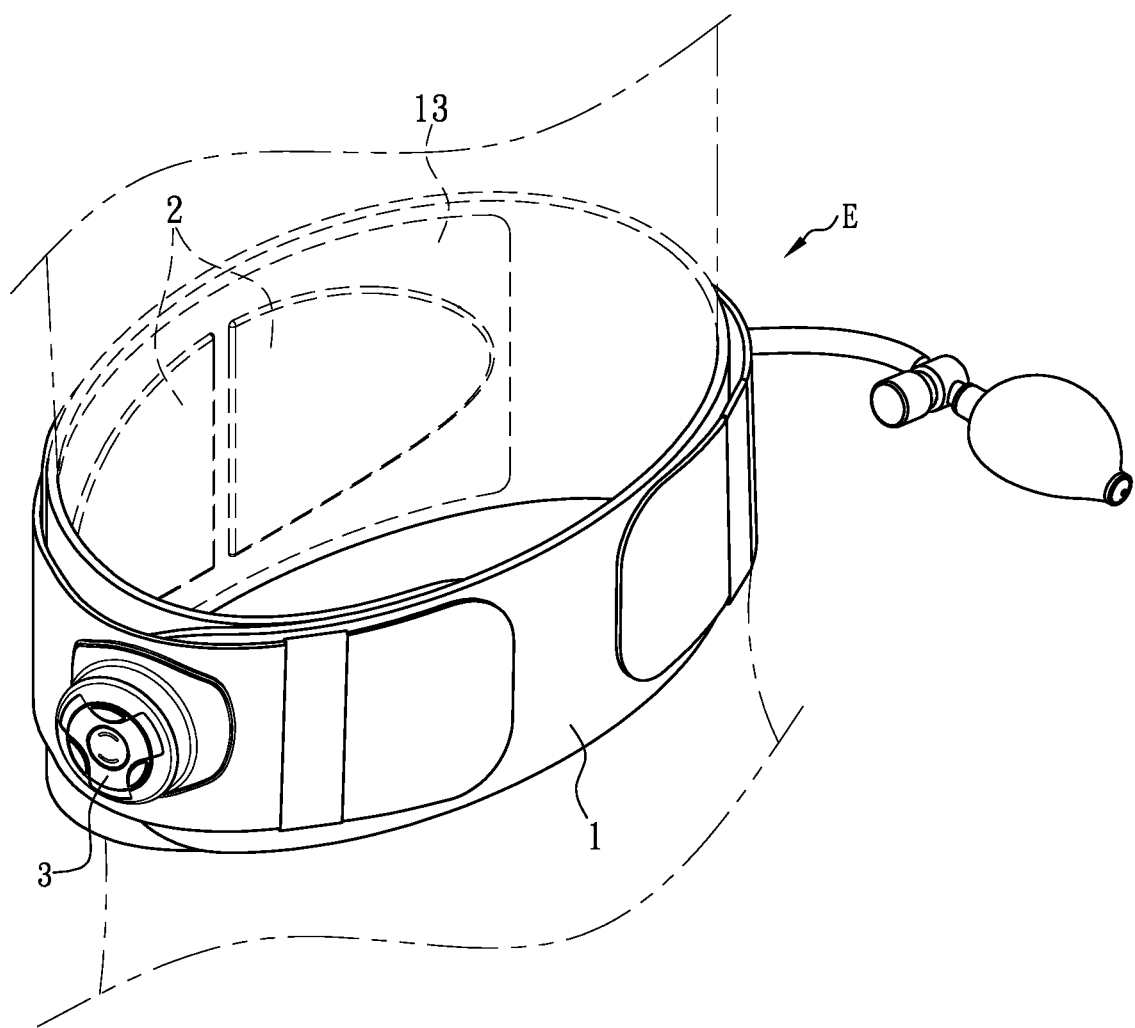
FIG. 14 is a perspective view of a body joint support device for the waist of a user according to certain embodiments of the present disclosure.
Figure 15:
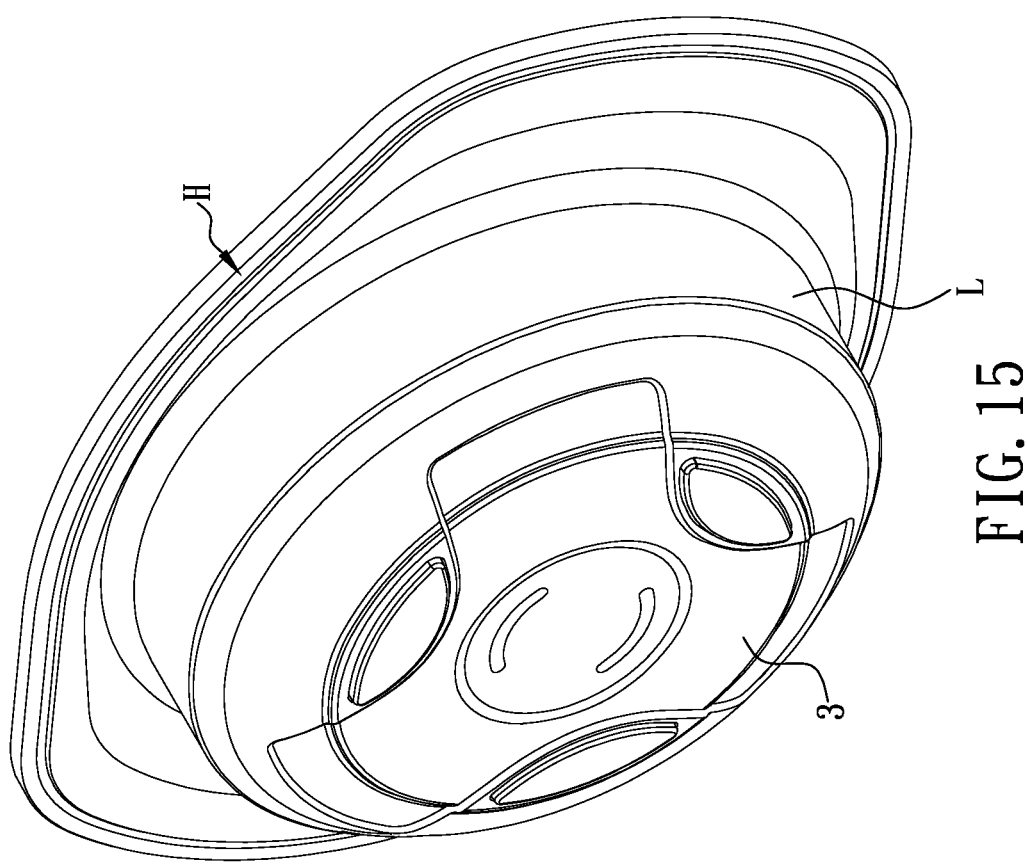
FIG. 15 is an assembled view showing a control device being harnessed in a holder by a secure releasable locking mechanism according to certain embodiments of the present disclosure.
Figure 16:
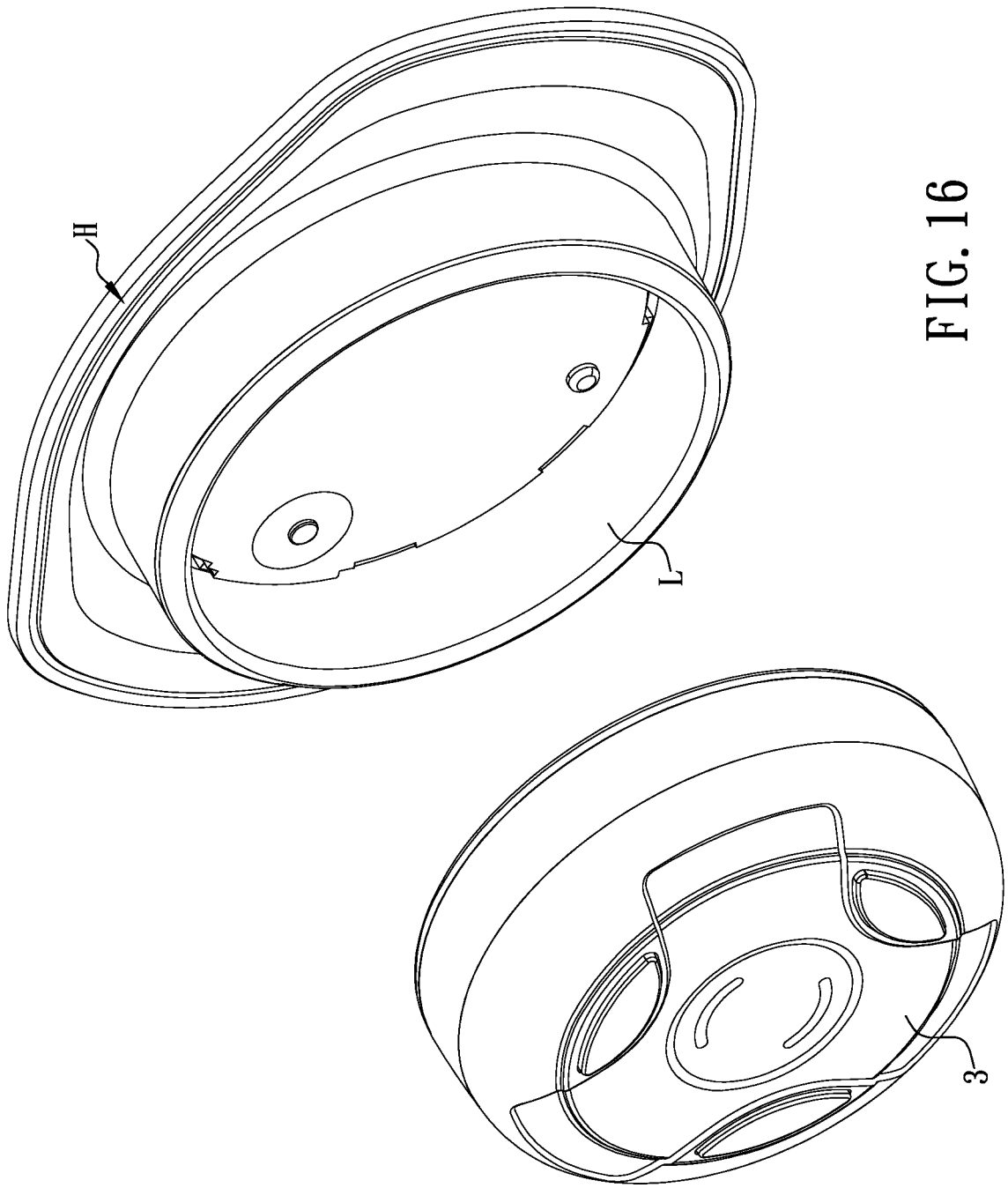
FIG. 16 is an exploded view of the assembly of the control device and the holder shown in FIG. 15 according to certain embodiments of the present disclosure.
Figure 17:
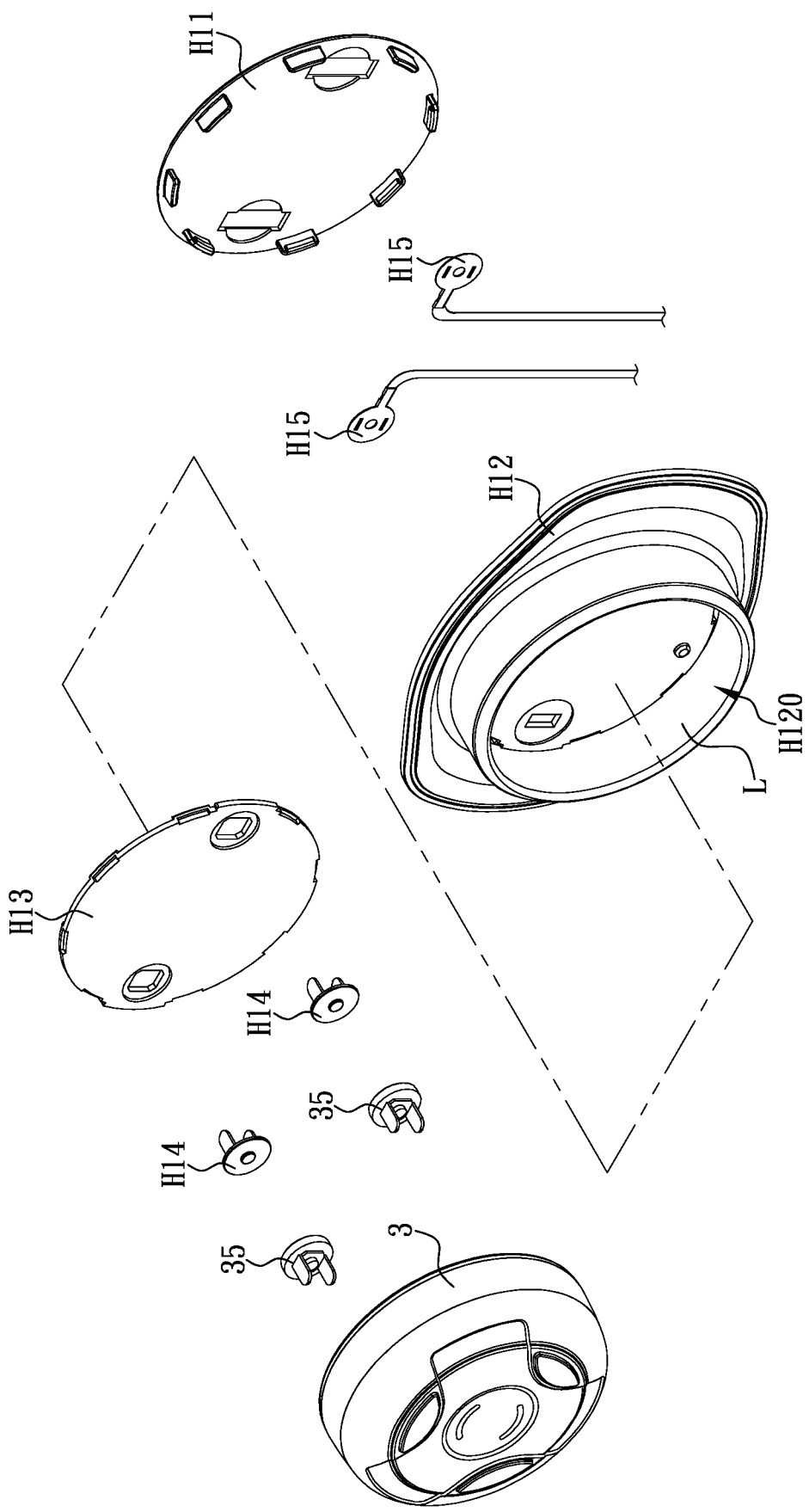
FIGS. 17 and 18 are exploded views showing the detailed components of the control device and the holder shown in FIG. 15 according to certain embodiments of the present disclosure.
Figure 18:
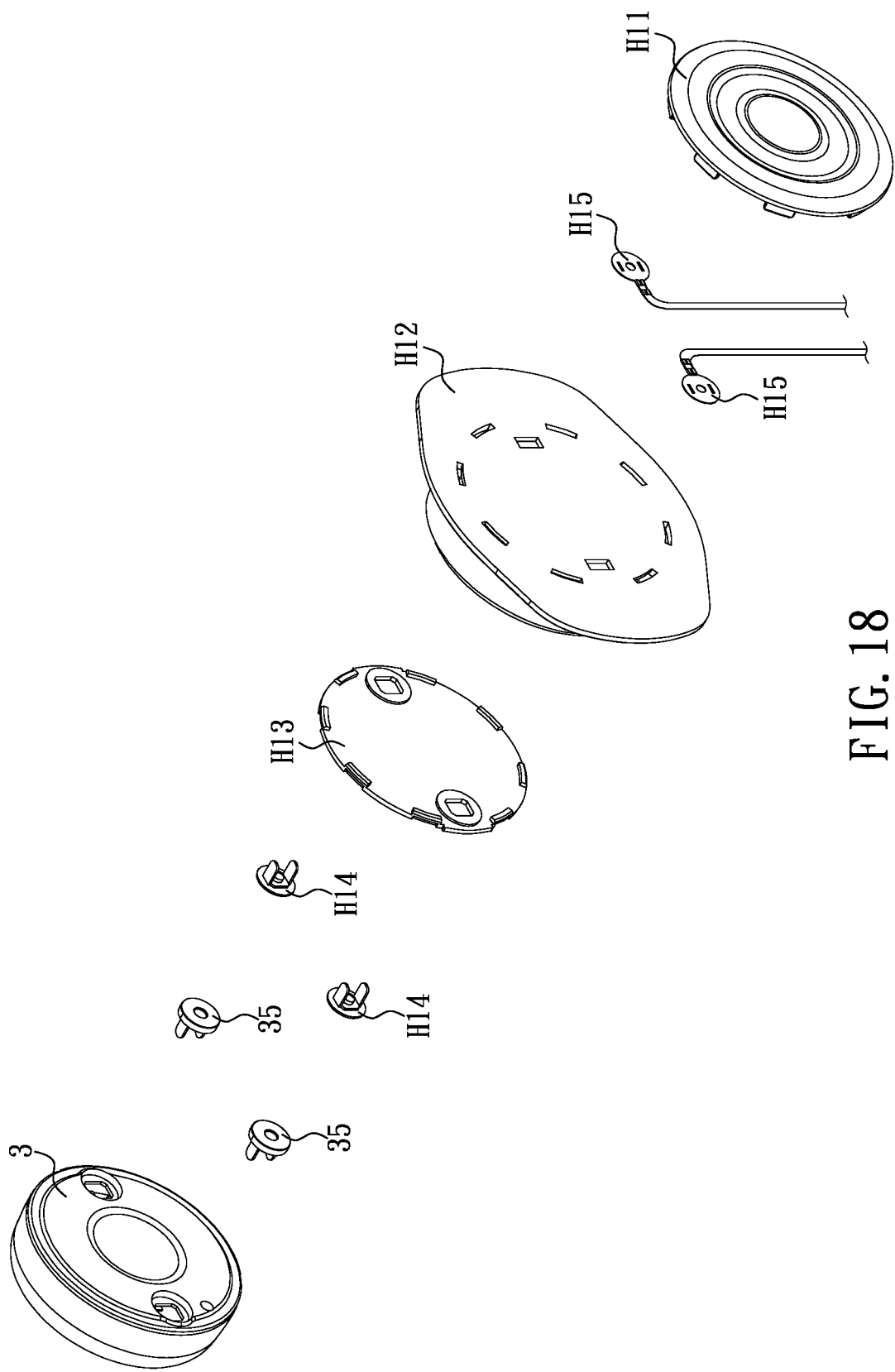

In the embodiments of the covering structure 1 including at least one elastic material, as the elasticity of the covering structure 1 contributes heavily to the effect of pressing the covering structure 1 tightly against the skin surface, the contour or shape of the covering structure 1 can change based on and adapt to the shapes of different body joints, and the covering structure 1 can be manufactured to be in shapes or include further components that adapt to the shapes of different body joints. For example, as shown in FIG. 9, the body joint support device E is in a configuration to be sleeved at an elbow joint. As shown in FIG. 10, the body joint support device E is in a configuration to be sleeved at a shoulder joint. As shown in FIG. 11, the body joint support device E is in a configuration to be sleeved at a knee joint. As shown in FIG. 12, the body joint support device E is in a configuration to be sleeved on a wrist joint. Referring to FIGS. 13 and 14, in certain embodiments, the body joint support device E can be in a configuration to be applied to a body part that is not limited to body joints. Referring to FIG. 13, the body joint support device E is in a configuration to be sleeved on a calf. Referring to FIG. 14, the body joint support device E can be in a configuration to be wrapped around the waist of a user, and be arranged therein with at least one airbag 13, electrode pad unit(s) 2 and an inflating device 14. The electrode pad unit(s) 2 can be disposed on and in front of the airbag 13 so as to be pressed tighter against the skin of the user by being pressed by the airbag 13 inflated by the inflating device 14. In certain embodiments, the airbag 13 and electrode pad unit(s) 2 are arranged at a position that corresponds to the lower back of the user when the body joint support device E in the configuration of a waist belt is applied and wrapped around the waist of a user, so as to alleviate syndromes including lower back pain. However, the present disclosure is not limited thereto, and the position of the airbag 13 and electrode pad unit(s) 2 at the body joint support device E can be adjusted according to practical requirement. In certain embodiments, the inflating device 14 may include at least one hand press inflation pump, or an electric inflation pump.

With these configurations, when the user is alone by himself or herself, the user can easily adjust and move the position(s) of the electrode pad unit(s) 2 to any location needing electrotherapy and/or heat therapy by pulling the covering structure 1, which greatly improves the convenience in use.

The control device 3 can be held and positioned on the covering structure 1 by a holder 1 that is designed with a secure releasable locking mechanism L to enable the control device 3 to be released on demand from, that is, the control device 3 is configured to disengage from, or fixed on demand on the holder 1. For example, whenever the covering structure 1 needs to be washed in water, the control device 3 can be taken off from the holder H, so as to prevent damage to the control device 3. In certain embodiments, the holder H with the releasable locking mechanism L may be a harness with a releasable lock. The holder 11 is provided with electrical conductive connectors so the control device 3 and/or a battery pack provided therein or thereon can transmit their power to the electrode pad unit(s) 2 so that the electrode pad unit 2 can perform electrotherapy and/or heat therapy.

Referring to FIGS. 15-18, in certain embodiments, the holder H includes a base plate 1111, a positioning body H12, an inner plate H13, a plurality of electrical conductive connectors H14, and a plurality of conductive-wire connectors H15. The base plate H11 and the positioning body H12 can be assembled with each other. A rear surface of the base plate H11 can be provided with at least one hook-and-loop fasteners, so as to be attached on the covering structure 1. The positioning body H12 can be made of at least one elastic material, and formed with an accommodating slot 11120 on the front surface thereof. The inner plate H13 can be arranged on the bottom surface of the accommodating slot H120. The inner diameter of the accommodating slot 11120 can be slightly smaller than the outer diameter of the control device 3, for example, being smaller by 0.1% to 5% of the outer diameter of the control device 3, and the slot wall of the accommodating slot H120 can form the releasable locking mechanism L by, when the control device 3 is placed within the accommodating slot H120, expanding to a small extent, due to the flexibility of the accommodating slot H120, to wrap and abut firmly against the periphery of the control device 3, so as to position the control device 3 on the positioning body H12. When the positioned control device 3 is pulled outward from the positioning body H12 with a force that is greater than a force by friction that is exerted by the slot wall of the accommodating slot H120 (that is, the releasable locking mechanism L) to the control device 3, the control device 3 can be removed from the releasable locking mechanism L.

Referring again to FIGS. 15-18, the electrical conductive connectors H14 can be placed in the accommodating slot H120, and extend through, in sequence, the inner plate H13 and the bottom surface of the accommodating slot H120 and to the base plate H11. The conductive-wire connectors 1115 can be located between the positioning body H12 and the base plate H11, and electrically connected to the corresponding electrical conductive connectors 1114 respectively. Each of the conductive-wire connectors 1115 can be electrically connected with at least one external conductive wire, for example, the conductive wire 21. Further, the rear side of the control device 3 can be provided with a plurality of electrical conductive members 35. After the control device 3 is placed in the accommodating slot 1120, each of the electrical conductive members 35 can be electrically connected with a corresponding electrical conductive connectors 1114, so that the electric current (current pulse signals) outputted by the control device 3 can pass in sequence through the electrical conductive member 35 and the electrical conductive connectors H14 and be transmitted to the conductive-wire connector H15. However, in certain embodiments, the electrical conductive connector H14 and the conductive-wire connector H115 may be integrated into one piece, and the electrical conductive connector H14 can be electrically connected with an external conductive wire.

Figure 19:
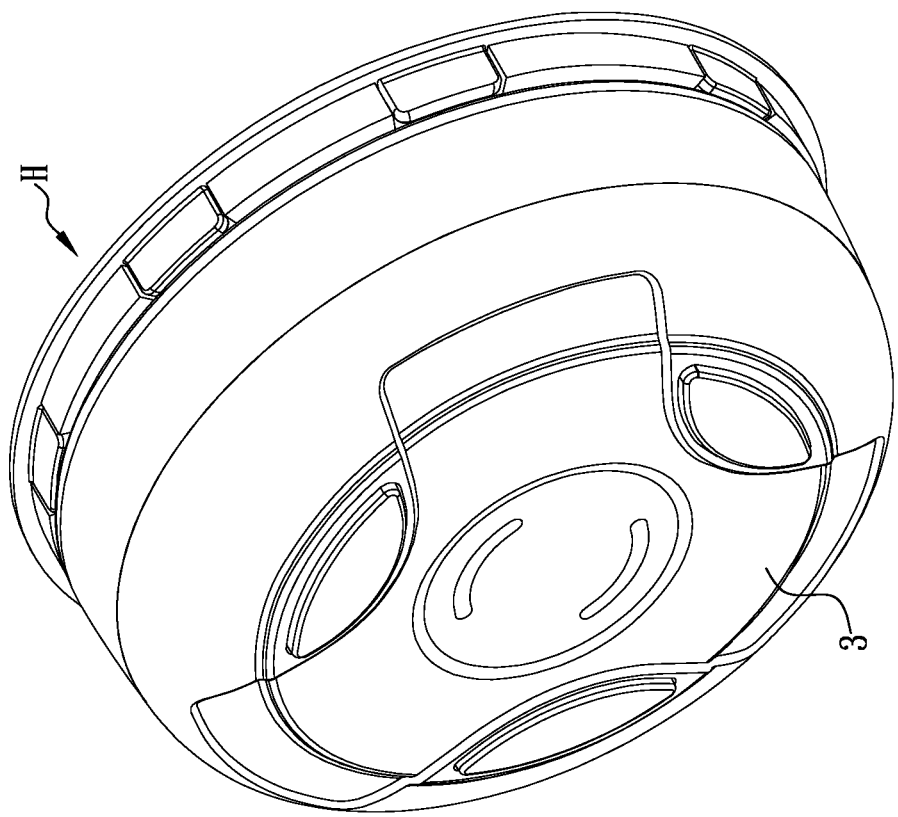
FIG. 19 is an assembled view showing the control device being harnessed in the holder according to certain other embodiments of the present disclosure.
Figure 20:
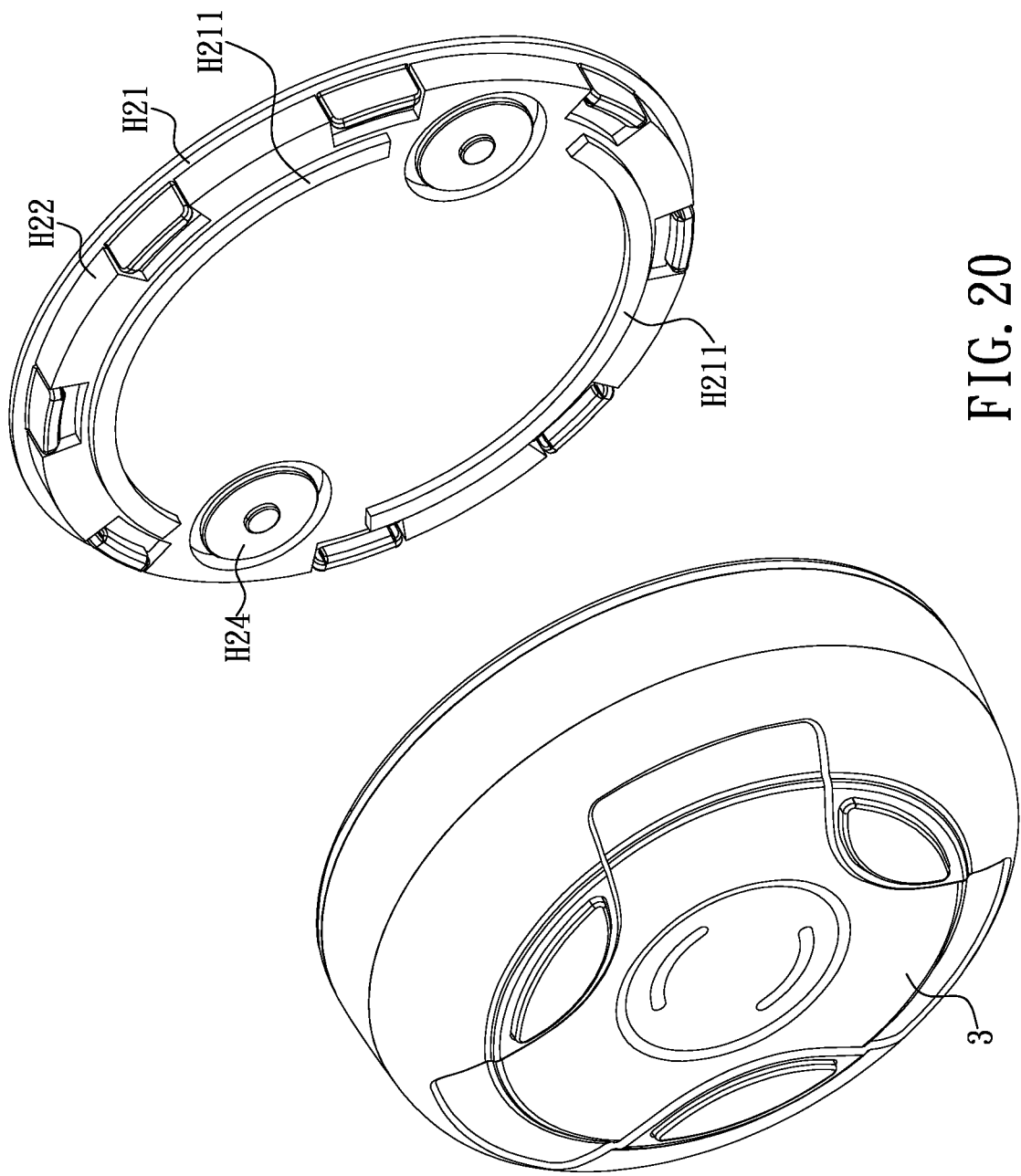
FIGS. 20 and 21 are exploded views of the assembly of the control device and the holder shown in FIG. 19 according to certain other embodiments of the present disclosure.
Figure 21:
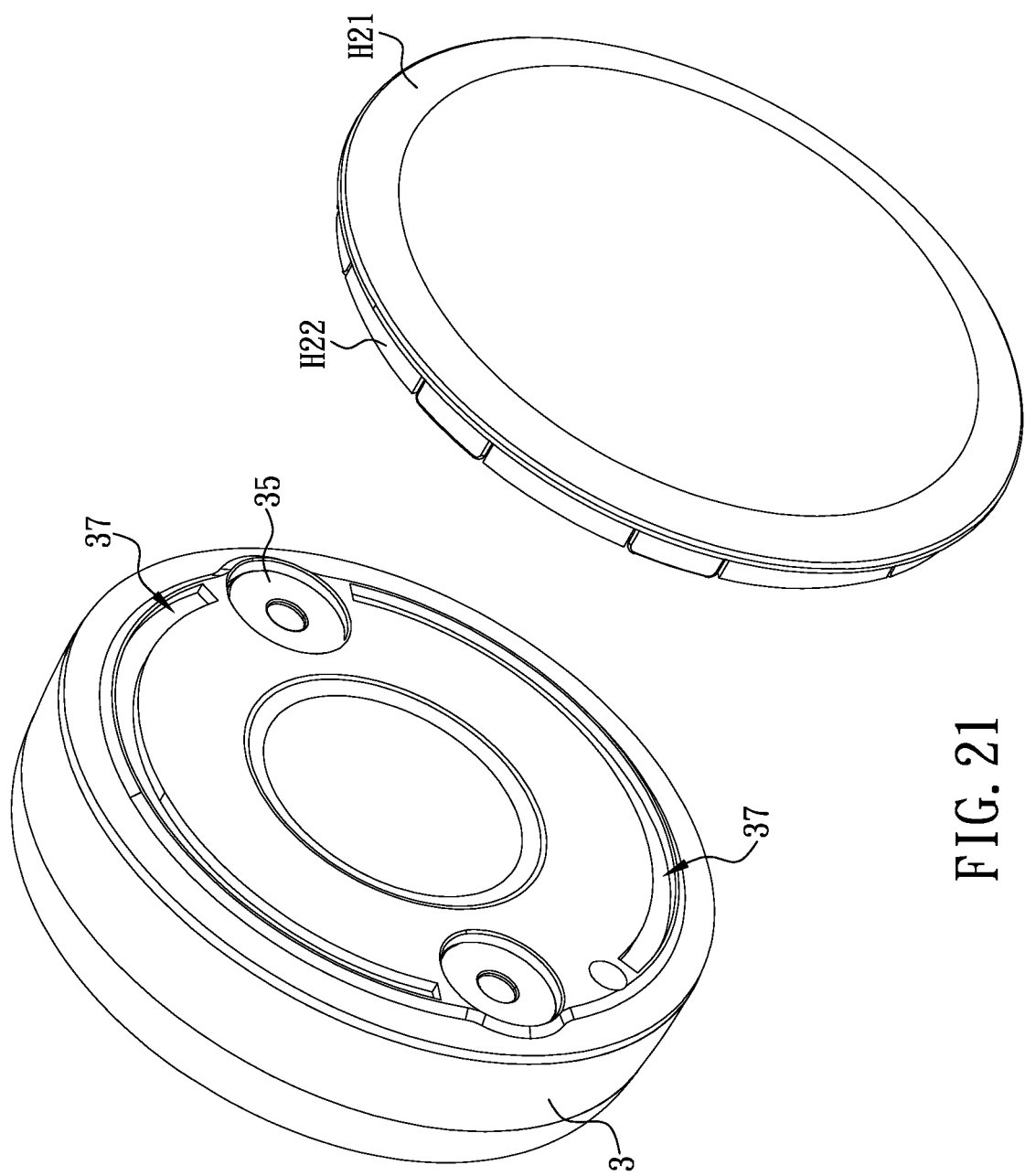

Referring to FIGS. 19-21, in certain embodiments, the holder H may include a base plate H21, a positioning body H22, and a plurality of electrical conductive connectors H24. The base plate 1121 and the positioning body 1122 can be assembled with each other, and the electrical conductive connectors H24 can be fixed on the positioning body H22. The front surface of the positioning body H22 can be protrudingly formed with at least one protruding rail H211 which serves as the releasable locking mechanism L. The rear surface of the control device 3 can be formed with at least one groove 37. The width and/or length of the groove 37 can be slightly smaller than the corresponding width and/or length of the protruding rail H211, for example, being smaller by 0.1% to 5% of the width of the protruding rail H211. When assembling the control device 3 to the holder 11, the protruding rail H211 can be inserted into a corresponding groove 37, and the electrical conductive member(s) 35 can at the same time be electrically connected with the electrical conductive connectors H24. When the positioned control device 3 is pulled outward from the positioning body H22 with a force that is greater than the clamping force between the protruding rail(s) H211 and the corresponding groove(s) 37, the control device 3 can be removed from the releasable locking mechanism L.

Figure 22:
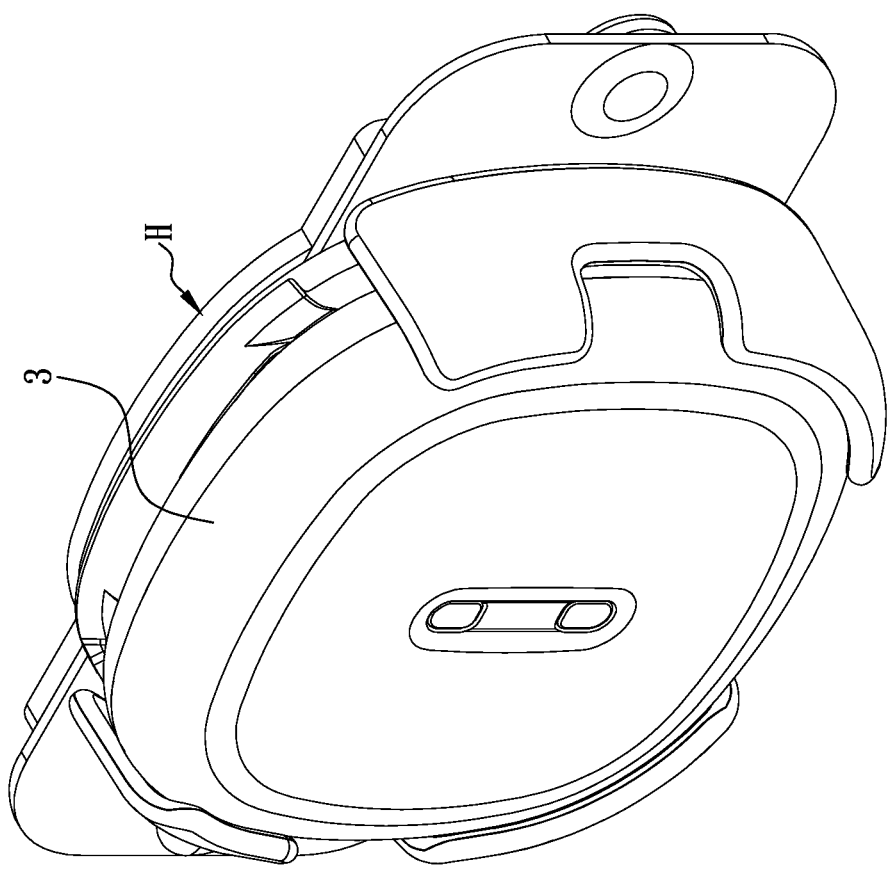
FIG. 22 is an assembled view showing the control device being harnessed in the holder according to yet certain other embodiments of the present disclosure.
Figure 23:
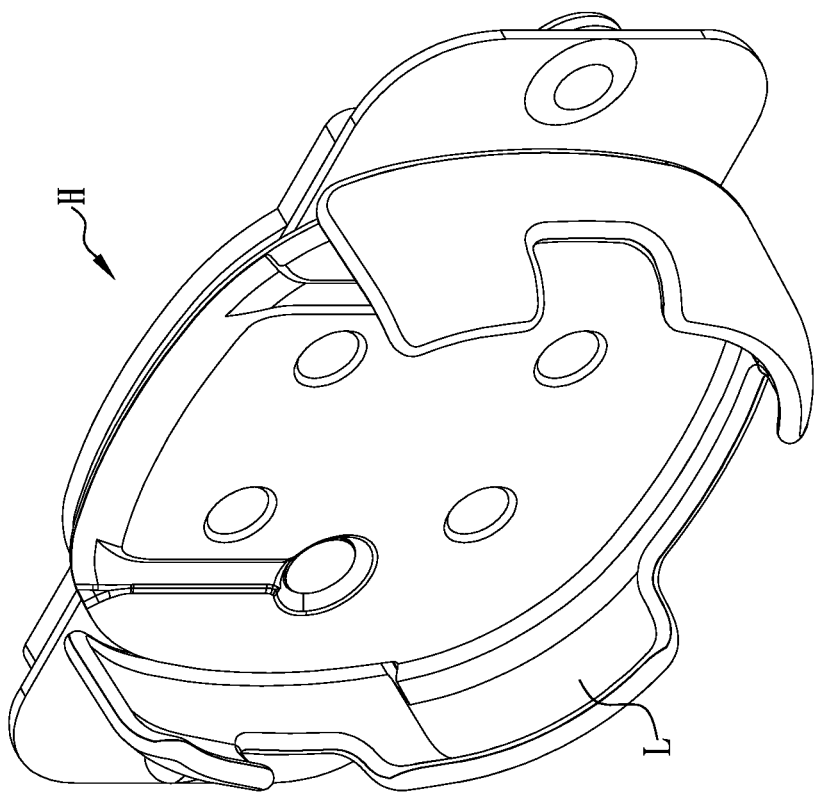
FIG. 23 is an exploded view of the assembly of the control device and the holder shown in FIG. 22 according to yet certain other embodiments of the present disclosure.
Figure 23:
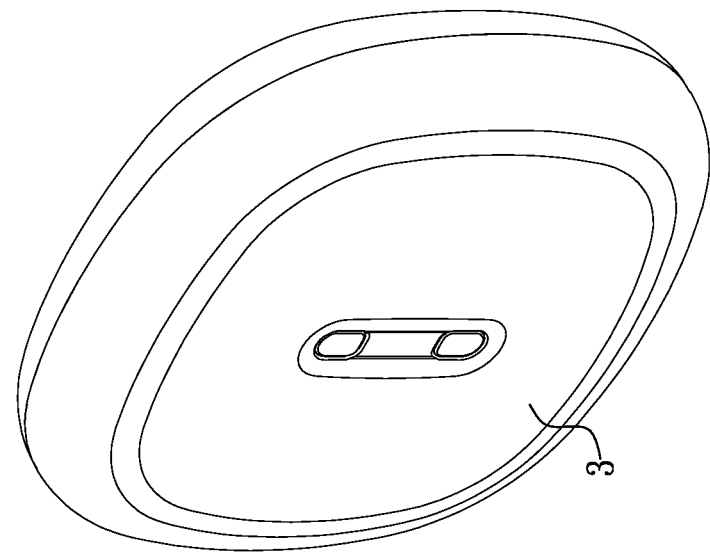
Figure 24:
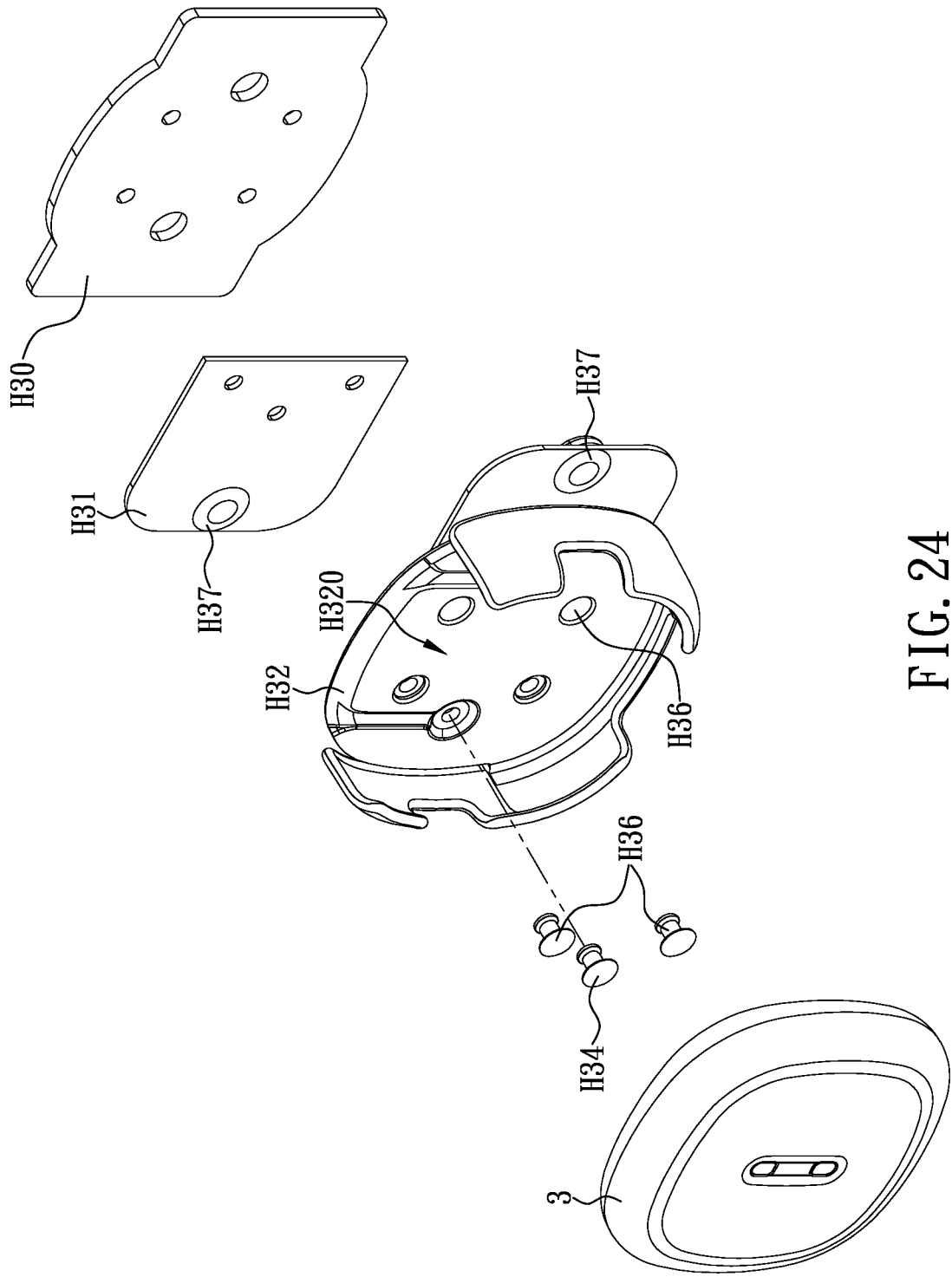
FIG. 24 is an exploded view showing the detailed components of the holder according to yet certain other embodiments of the present disclosure.

Referring to FIGS. 22-24, in certain embodiments, the holder H may include at least one base plate H31, a positioning body H32, and a plurality of electrical conductive connectors H34. The front side of the base plate 131 can abut against the rear side of the positioning body H32, and the rear side of the base plate H31 can abut against a connection plate 1H30 (for example, at least one hook-and-loop fastener). The base plate H31, the positioning body H32 and the connection plate H30 can be assembled into one piece through a plurality of fastening members H36. The front side of the positioning body H32 is formed with an accommodating room 11320, and the control device 3 can be placed in the accommodating room H320, with the surrounding wall defining and of the accommodating slot H320 forming the releasable locking mechanism L. A part of the base plate H31 that is not blocked by the positioning body H32 when the positioning body 1132 and the base plate 1131 are assembled can be provided with at least one fixing member H37 (for example, a button). The fixing member 1137 can be buckled with a corresponding fixing member on the covering structure 1, so that the holder H can be more firmly positioned on the covering body 1.

Once the control device 3 is locked in place within the holder H, the user can move about and the control device 3 will not be displaced. The secure releasable locking mechanism L works to hold the control device 3 securely on the covering structure 1, and to not allow the control device 3 to dislodge from the covering structure 1 even if the user is moving while working on the job or playing sport.

When the covering structure 1 needs to be washed, the releasable locking mechanism L can be unlocked to release and remove the control device 3 from the holder H before the covering structure 1 is washed in water, so as to prevent damage to the components within the control device 3. In certain embodiments, the releasable locking mechanism L can be disposed directly on the covering structure 1 without the holder H, and is electrically connected to the electrode pad unit(s) 2 to transmit current to the electrode 2S pad unit(s) 2.

Figure 25A:
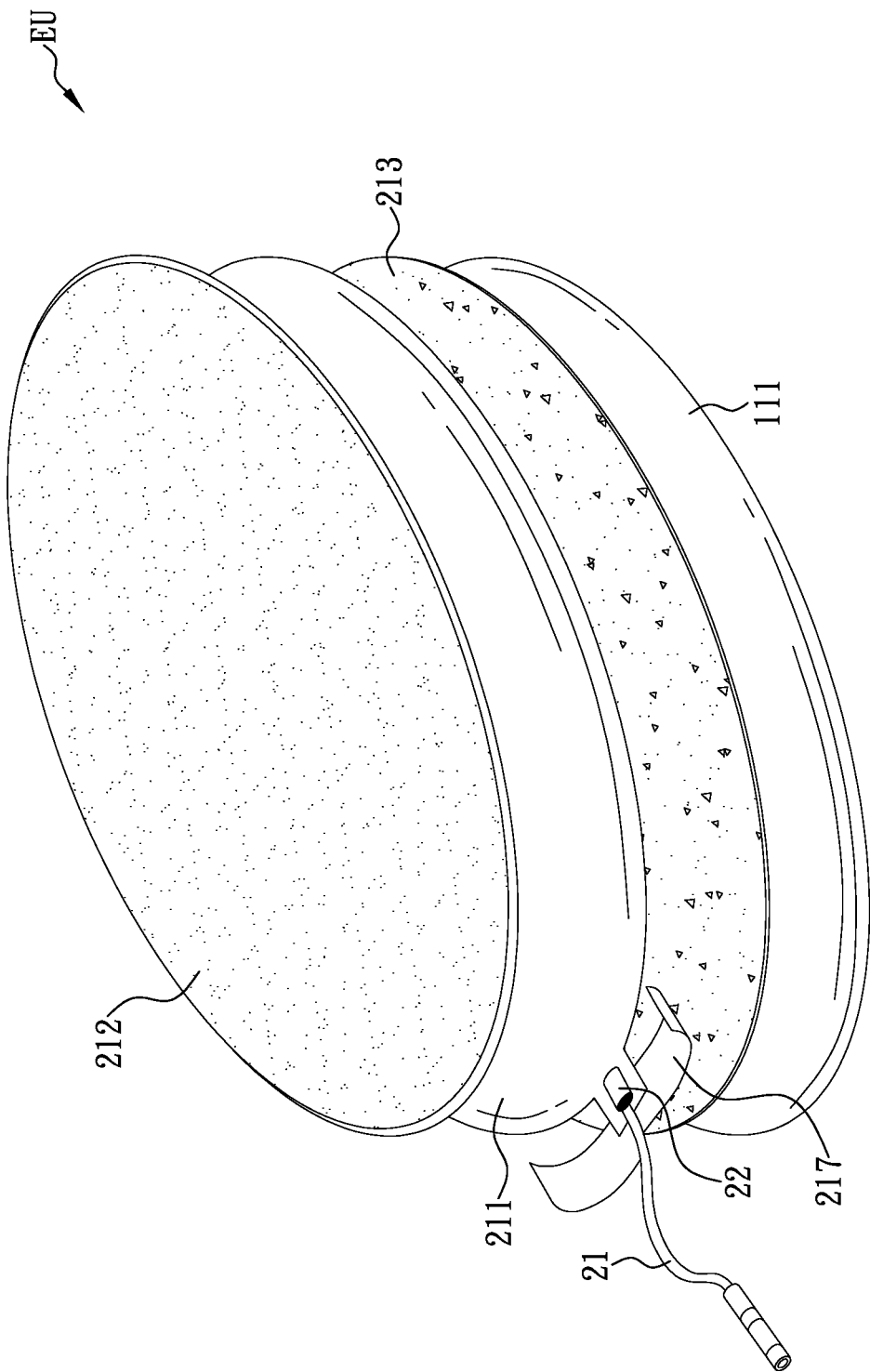
FIG. 25A is a schematic view of an electrode pad unit configured as an electrotherapy unit according to certain embodiments of the present disclosure.
Figure 25B:
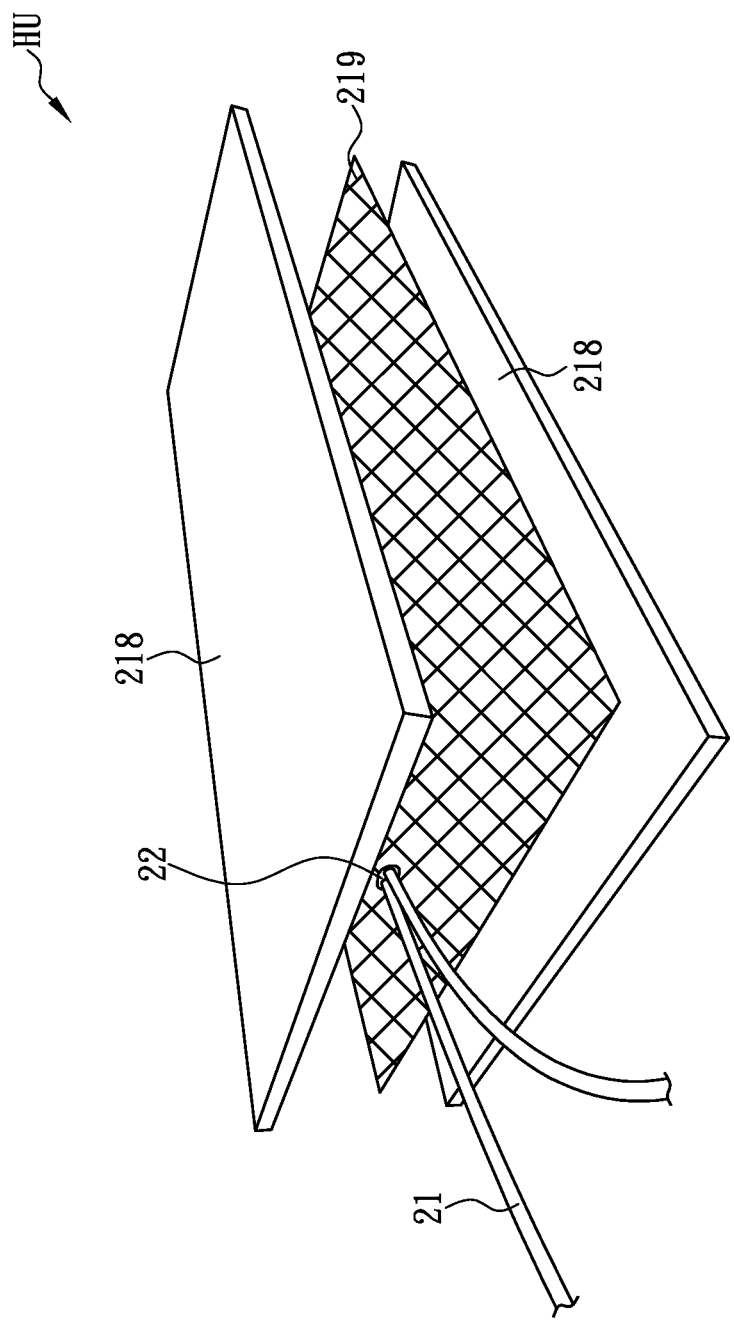
FIG. 25B is a schematic view of an electrode pad unit configured as a heat therapy unit according to certain embodiments of the present disclosure.

Referring to FIG. 25A, in certain embodiments, an electrode pad unit 2 can be configured as an electrotherapy unit EU. The electrotherapy unit EU can include a conductive layer 211, optionally a cover layer 212, and an adhesion layer 213. The conductive layer 211 may be a layer of conductive fibers, conductive film, conductive cloth, aluminum foil, or a mixture thereof, or be made of other conductive materials. One side of the conductive layer 211 can be disposed with the cover layer 212 (for example, a layer of fabric, or a layer of conductive gel), while the other side of the conductive layer 211 can be disposed with the adhesion layer 213. The conductive layer 211 can be electrically connected to a metal member 22, and the metal member 22 can be electrically connected to the conductive wire 21. An insulative band 217 can be wound around and fix the metal member 22 and the conductive wire 21. The adhesion layer 213 (for example, a layer of glue) can be fixed to the first sheet body 111, so that for a user to use the body joint support device E, as long as the conductive layer 211, or if the cover layer 212 exists, the cover layer 212, is abutted against his or her body joint, and the conductive wire 21 is electrically connected to the control device 3, electric power from the control device 3 such as a TENS or EMS device can be received by the electrode pad unit 2, and the electrode pad unit 2 can output electrical stimulation to the body joint of a user to achieve the effect of electrotherapy. However, the present disclosure is not limited thereto. In certain embodiments, when the cover layer 212 is omitted, the conductive layer 211 is in direct contact with the skin. The adhesion layer 213 may include fabric such as nonwoven or cotton fabric, and can be connected with a conductive sheet such as an aluminum foil, so as to be better connected to the first sheet body 111.

Referring to FIG. 2511, in certain embodiments, an electrode pad unit 2 can be configured as a heat therapy unit 111U. The heat therapy unit HU can include two cushion layers 218 (for example, being made of non-woven fabric) and a heat-generating layer 219. The heat-generating layer 219 can be made of metal material (e.g., iron-chromium-aluminum alloy wires, nickel-chromium alloy wires, etc.), graphene, carbon fiber material, or other electrothermal materials, etc., so as to generate heat when electric current passes therethrough. The heat-generating layer 219 can be sandwiched between the two cushion layers 218, and the outer surface of one of the cushion layers 218 can be fixated on the corresponding first sheet body 111. The heat-generating layer 219 can be electrically connected with the metal member 22 to receive electric power from the control device 3 through the conductive wire 21, so that the electrode pad unit 2 generates heat that is conducted away through the cushion layers 218, and heats the body joint of the user to relax blood vessels and increase local blood circulation and the rate of metabolism, such that inflammatory substances are quickly expelled from the human body and self-healing abilities of the muscle tissue can be improved. At the same time, warm compresses can increase soft tissue resilience and reduce muscle spasms, so as to relieve one's pain and relax one's emotions. In certain embodiments, the cushion layers 218 may be omitted, and the heat-generating layer 219 is in direct contact with the skin.

Figure 25C:
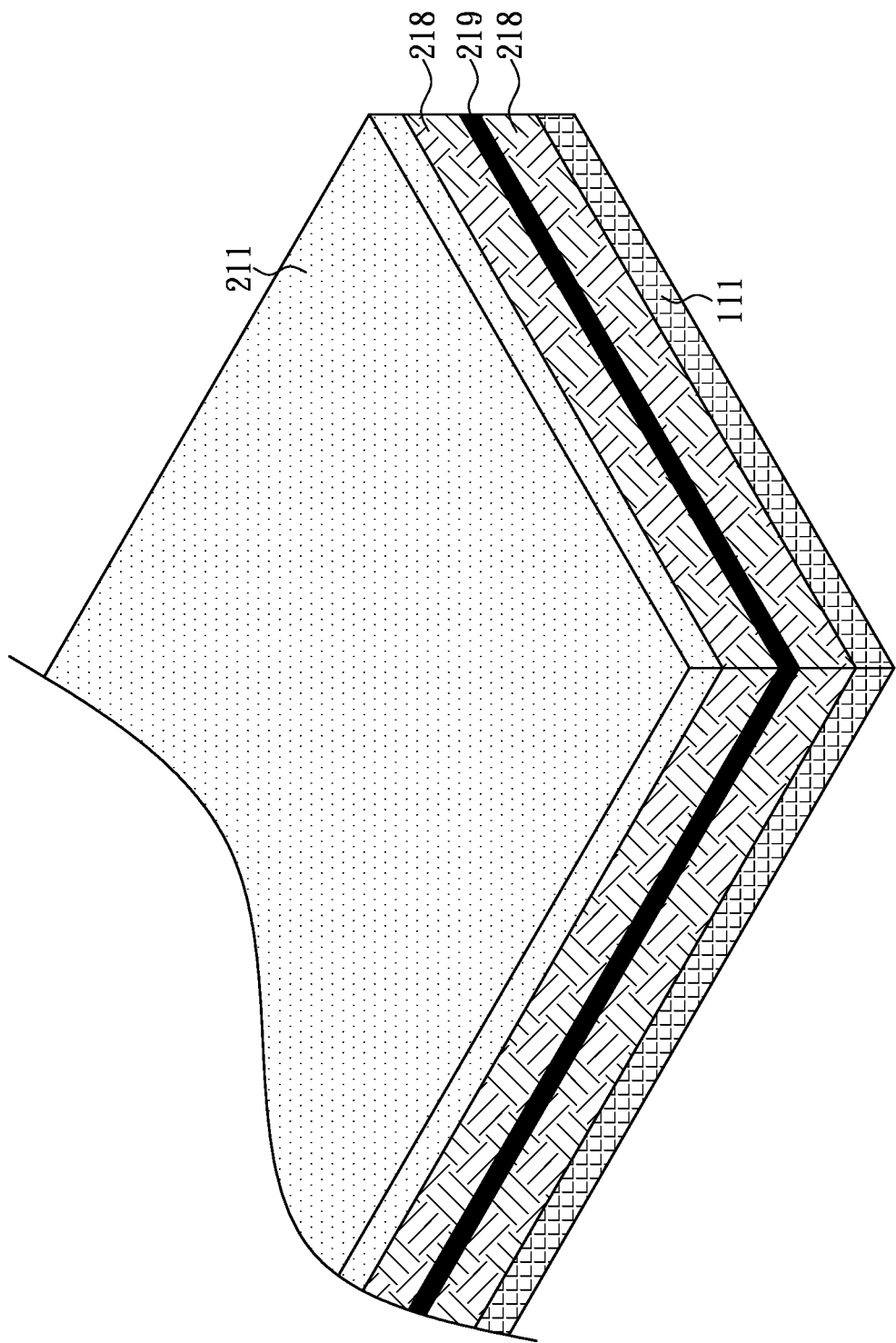
FIG. 25C is a schematic view of an electrode pad unit configured as a combined electrotherapy-heat therapy unit according to certain embodiments of the present disclosure.

Referring to FIG. 25C, in certain embodiments, an electrode pad unit 2 can be configured as a combined electrotherapy-heat therapy unit. The combined electrotherapy-heat therapy unit can be formed by stacking the foregoing electrotherapy unit EU and heat therapy unit HU. For example, a heat-generating layer 219 is provided between two cushion layers 218, and the outer surface of one of the cushion layers 218 can be covered with the conductive layer 211, such as a layer of conductive fiber. The heat-generating layer 219 and the conductive layer 211 can receive electric power from the control device 3 through the same or different metal members 22. The conductive layer 211 can output electrical stimulation to the body joint of the user, while the heat-generating layer 219 can generate heat which passes through the cushion layers 218 and the conductive layer 211 to heat the body joint of the user.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:
1. A body joint support device, comprising:
 a covering structure configured to be worn at at least one body joint and press a skin of the body joint that is in a bending state against an inner surface of the covering structure by a pressing force exerted by the covering structure;

at least one electrode pad unit disposed on the inner surface of the covering structure and configured to abut against the skin of the body joint through the pressing force; and a control device configured to be fixed on the covering structure and transmit current to the electrode pad unit for the electrode pad unit to transmit current to stimulate or to heat muscle, wherein the covering structure comprises a covering body having an inner surface disposed with the electrode pad unit, and at least one airbag located in the covering body wherein the airbag has an opening to allow for flexing of the body joint, and the electrode pad unit only partially overlaps in position the airbag with both of two opposite ends of the electrode pad unit not overlapping in position the airbag.

2. The body joint support device according to claim 1, wherein the control device is disposed on an outer surface of the covering body, the at least one airbag is configured to expand along a direction toward the inner surface of the covering body so that the inner surface of the covering body exerts the pressing force to the skin of the body joint, and the covering structure further comprises:

at least one inflating device configured to be connected to the airbag and inflate or deflate the airbag to change an expansion degree or deflation degree of the airbag; and at least one adjusting strap having one end connected to the covering body and another end provided with a fixation portion configured to be fixed on the outer surface of the covering body and be pulled to press the inner surface of the covering body against the skin of the body joint.

3. The body joint support device according to claim 2, wherein the covering body comprises a first sheet body and a second sheet body, the airbag is located between the first sheet body and the second sheet body, the electrode pad unit is disposed on the first sheet body, and the control device and the adjusting strap are disposed on the second sheet body.

4. The body joint support device according to claim 3, further comprising at least one angle adjustable support member including at least two plate bodies having an adjustable fixed angle therebetween, each having one end configured to be inserted into a corresponding slot formed on the outer surface of the covering body.

5. The body joint support device according to claim 2, wherein the inflating device comprises at least one air valve and an inflating member configured to be connected to the airbag through the air valve and inflate or deflate the airbag.

6. The body joint support device according to claim 1, wherein the covering structure comprises at least one elastic material and is configured to, when worn at the body joint, abut against the skin of the body joint by the elasticity of the covering structure.

7. The body joint support device according to claim 6, wherein the covering structure is in a cylindrical shape and configured to be sleeved at the body joint.

8. The body joint support device according to claim 1, wherein the covering body comprises a sheet body, a maximum height of the sheet body along the longitudinal axis of the sheet body ranges between 31.1 and 37.9 cm, the sheet body has a first extension portion, a second extension portion opposite to the first extension portion, a third extension portion and a fourth extension portion opposite to the third extension portion, a length from a free end of the first extension portion to a free end of the second extension portion along an axis perpendicular or substantially perpendicular to the longitudinal axis of the sheet body ranges between 50.0 and 58.2 cm, and a length from a free end of the third extension portion to a free end of the fourth extension portion along an axis perpendicular or substantially perpendicular to the longitudinal axis of the sheet body ranges between 44.3 and 52.1 cm.

9. The body joint support device according to claim 1, wherein the covering body comprises a sheet body, a maximum height of the sheet body along the longitudinal axis of the sheet body ranges between 31.1 and 37.9 cm, the sheet body has a first extension portion, a second extension portion opposite to the first extension portion, a third extension portion and a fourth extension portion opposite to the third extension portion, a length from a free end of the first extension portion to a free end of the second extension portion along an axis perpendicular or substantially perpendicular to the longitudinal axis of the sheet body ranges between 43.0 and 50.0 cm, and a length from a free end of the third extension portion to a free end of the fourth extension portion along an axis perpendicular or substantially perpendicular to the longitudinal axis of the sheet body ranges between 37.7 and 44.3 cm.

10. The body joint support device according to claim 8, wherein the covering structure further comprises at least two adjusting straps, including a longer adjusting strap and a shorter adjusting strap, a length of the longer adjusting strap is between 57.6 and 70.4 cm, and a length of the shorter adjusting strap is between 51.3 and 62.7 cm.

11. The body joint support device according to claim 9, wherein the covering structure further comprises at least two adjusting straps, including a longer adjusting strap and a shorter adjusting strap, a length of the longer adjusting strap is between 57.6 and 70.4 cm, and a length of the shorter adjusting strap is between 51.3 and 62.7 cm.

12. The body joint support device according to claim 1, wherein the control device comprises:

a direct current (DC) power supply unit configured to provide power for operation of the control device;

a control unit configured to generate and transmit a plurality of control signals; and a pulse output circuit electrically connected to the control unit and configured to:

receive power from the DC power supply unit and the control signals from the control unit;

form at least one current pulse signal having a predetermined waveform based on the characteristics of at least one of the control signals; and transmit the current pulse signal to the electrode pad unit.

13. The body joint support device according to claim 2, wherein the control device comprises:

a direct current (DC) power supply unit configured to provide power for operation of the control device;

a control unit configured to generate and transmit a plurality of control signals; and a pulse output circuit electrically connected to the control unit and configured to:

receive power from the DC power supply unit and the control signals from the control unit;

form at least one current pulse signal having a predetermined waveform based on the characteristics of at least one of the control signals; and transmit the current pulse signal to the electrode pad unit.

14. The body joint support device according to claim 3, wherein the control device comprises:

a direct current (DC) power supply unit configured to provide power for operation of the control device;

a control unit configured to generate and transmit a plurality of control signals; and a pulse output circuit electrically connected to the control unit and configured to:
- receive power from the DC power supply unit and the control signals from the control unit;
- form at least one current pulse signal having a predetermined waveform based on the characteristics of at least one of the control signals; and
- transmit the current pulse signal to the electrode pad unit.

15. The body joint support device according to claim 4, wherein the control device comprises:
- a direct current (DC) power supply unit configured to provide power for operation of the control device;
- a control unit configured to generate and transmit a plurality of control signals; and
- a pulse output circuit electrically connected to the control unit and configured to:
  - receive power from the DC power supply unit and the control signals from the control unit;
  - form at least one current pulse signal having a predetermined waveform based on the characteristics of at least one of the control signals; and
  - transmit the current pulse signal to the electrode pad unit.

16. The body joint support device according to claim 5, wherein the control device comprises:
- a direct current (DC) power supply unit configured to provide power for operation of the control device;
- a control unit configured to generate and transmit a plurality of control signals; and
- a pulse output circuit electrically connected to the control unit and configured to:
  - receive power from the DC power supply unit and the control signals from the control unit;
  - form at least one current pulse signal having a predetermined waveform based on the characteristics of at least one of the control signals; and
  - transmit the current pulse signal to the electrode pad unit.

17. The body joint support device according to claim 6, wherein the control device comprises:
- a direct current (DC) power supply unit configured to provide power for operation of the control device;
- a control unit configured to generate and transmit a plurality of control signals; and
- a pulse output circuit electrically connected to the control unit and configured to:
  - receive power from the DC power supply unit and the control signals from the control unit;
  - form at least one current pulse signal having a predetermined waveform based on the characteristics of at least one of the control signals; and
  - transmit the current pulse signal to the electrode pad unit.

18. The body joint support device according to claim 7, wherein the control device comprises:
- a direct current (DC) power supply unit configured to provide power for operation of the control device;
- a control unit configured to generate and transmit a plurality of control signals; and
- a pulse output circuit electrically connected to the control unit and configured to:
  - receive power from the DC power supply unit and the control signals from the control unit;
  - form at least one current pulse signal having a predetermined waveform based on the characteristics of at least one of the control signals; and
  - transmit the current pulse signal to the electrode pad unit.

19. The body joint support device according to claim 8, wherein the control device comprises:
- a direct current (DC) power supply unit configured to provide power for operation of the control device;
- a control unit configured to generate and transmit a plurality of control signals; and
- a pulse output circuit electrically connected to the control unit and configured to:
  - receive power from the DC power supply unit and the control signals from the control unit;
  - form at least one current pulse signal having a predetermined waveform based on the characteristics of at least one of the control signals; and
  - transmit the current pulse signal to the electrode pad unit.

20. The body joint support device according to claim 9, wherein the control device comprises:
- a direct current (DC) power supply unit configured to provide power for operation of the control device;
- a control unit configured to generate and transmit a plurality of control signals; and
- a pulse output circuit electrically connected to the control unit and configured to:
  - receive power from the DC power supply unit and the control signals from the control unit;
  - form at least one current pulse signal having a predetermined waveform based on the characteristics of at least one of the control signals; and
  - transmit the current pulse signal to the electrode pad unit.

* * * * *